US010687849B2

(12) United States Patent
Kassab et al.

(10) Patent No.: US 10,687,849 B2
(45) Date of Patent: Jun. 23, 2020

(54) MATERIALS AND METHODS OF USING THE SAME TO IMPROVE STRUCTURAL INTEGRITY OF A WALL OF A MAMMALIAN LUMINAL ORGAN

(71) Applicants: Ghassan S. Kassab, La Jolla, CA (US); Matthew Phillips, Carlsbad, CA (US)

(72) Inventors: Ghassan S. Kassab, La Jolla, CA (US); Matthew Phillips, Carlsbad, CA (US)

(*) Notice: Subject to any disclaimer, the term of this patent is extended or adjusted under 35 U.S.C. 154(b) by 150 days.

(21) Appl. No.: 15/570,222

(22) PCT Filed: Apr. 28, 2016

(86) PCT No.: PCT/US2016/029893
§ 371 (c)(1),
(2) Date: Oct. 27, 2017

(87) PCT Pub. No.: WO2016/176515
PCT Pub. Date: Nov. 3, 2016

(65) Prior Publication Data
US 2018/0125532 A1 May 10, 2018

Related U.S. Application Data

(60) Provisional application No. 62/312,642, filed on Mar. 24, 2016, provisional application No. 62/293,187, (Continued)

(51) Int. Cl.
A61B 17/34 (2006.01)
A61M 25/00 (2006.01)
(Continued)

(52) U.S. Cl.
CPC .......... A61B 17/3478 (2013.01); A61B 17/12 (2013.01); A61K 9/0019 (2013.01);
(Continued)

(58) Field of Classification Search
CPC ...... A61B 17/3478; A61B 2017/00247; A61B 2017/308; A61B 17/00491; A61B 17/12;
(Continued)

(56) References Cited

U.S. PATENT DOCUMENTS 5,882,332 A 3/1999 Wijay
7,744,583 B2 6/2010 Seifert et al.
(Continued)

FOREIGN PATENT DOCUMENTS

WO 2014/018463 A1 1/2014

OTHER PUBLICATIONS

International Searching Authority, International Search Report, PCT/US2016/029093, dated Aug. 5, 2016.
(Continued)

Primary Examiner — Imani N Hayman
(74) Attorney, Agent, or Firm — Reichel Stohry Dean LLP; Mark C. Reichel; Natalie J. Dean

(57) ABSTRACT

Materials and methods of using the same to improve structural integrity of a wall of a mammalian luminal organ. In an exemplary method of method for reinforcing a wall of a luminal organ, the method comprises the steps of inserting at least part of a needle into a blood vessel of a patient, advancing a distal end of the needle within the blood vessel to a location adjacent to a wall of a luminal organ of interest, piercing the wall of the luminal organ using the needle so that a tip of the needle is present within the wall of the luminal organ, injecting a substance through the needle and out of a distal portion of the needle so that at least some of the substance is present outside of the needle and inside of the wall of the luminal organ to reinforce the wall of the luminal organ.

20 Claims, 12 Drawing Sheets

Related U.S. Application Data filed on Feb. 9, 2016, provisional application No. 62/153,788, filed on Apr. 28, 2015.

(51) Int. Cl.
*A61M 25/04* (2006.01)
*A61B 17/12* (2006.01)
*A61K 9/00* (2006.01)
*A61B 17/00* (2006.01)
*A61B 17/30* (2006.01)
*A61B 17/22* (2006.01)

(52) U.S. Cl.
CPC ........ *A61M 25/0084* (2013.01); *A61M 25/04* (2013.01); *A61B 2017/00247* (2013.01); *A61B 2017/00778* (2013.01); *A61B 2017/22095* (2013.01); *A61B 2017/308* (2013.01); *A61M 2025/0089* (2013.01)

(58) Field of Classification Search
CPC ............ A61B 17/3401; A61B 17/3403; A61B 17/3415; A61B 18/02; A61B 18/14; A61B 2017/00026; A61B 2017/00044; A61B 2017/00084; A61B 2017/00778; A61B 2017/22095; A61B 2018/00291; A61M 25/0084; A61M 2025/0057; A61M 2025/0089; A61M 25/0026; A61M 25/0067; A61M 25/04; A61M 25/06; A61M 25/09; A61K 9/0019

See application file for complete search history.

(56) References Cited

U.S. PATENT DOCUMENTS

| | | |
|---|---|---|
| 8,328,752 B2 | 12/2012 | Kassab et al. |
| 2007/0106259 A1 | 5/2007 | Epstein et al. |
| 2010/0280493 A1 | 11/2010 | Nayak |
| 2013/0072855 A1 | 3/2013 | Sherry et al. |
| 2014/0052052 A1 | 2/2014 | Magana et al. |

OTHER PUBLICATIONS

International Searching Authority, Written Opinion of the International Searching Authority, PCT/US2016/29093, dated Aug. 5, 2016.

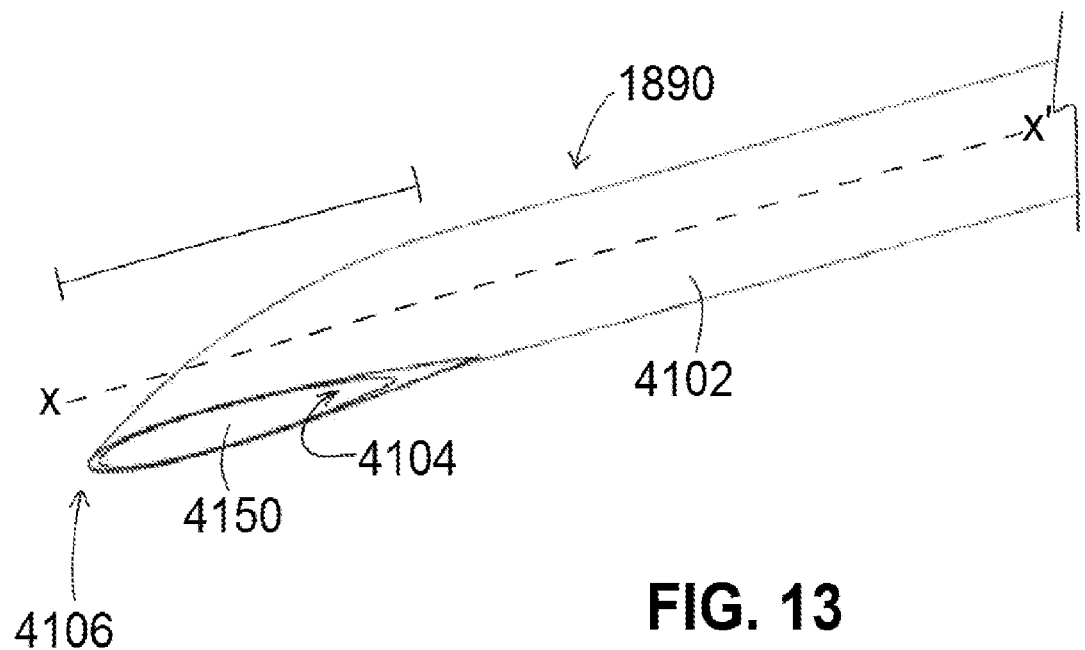
FIG. 13
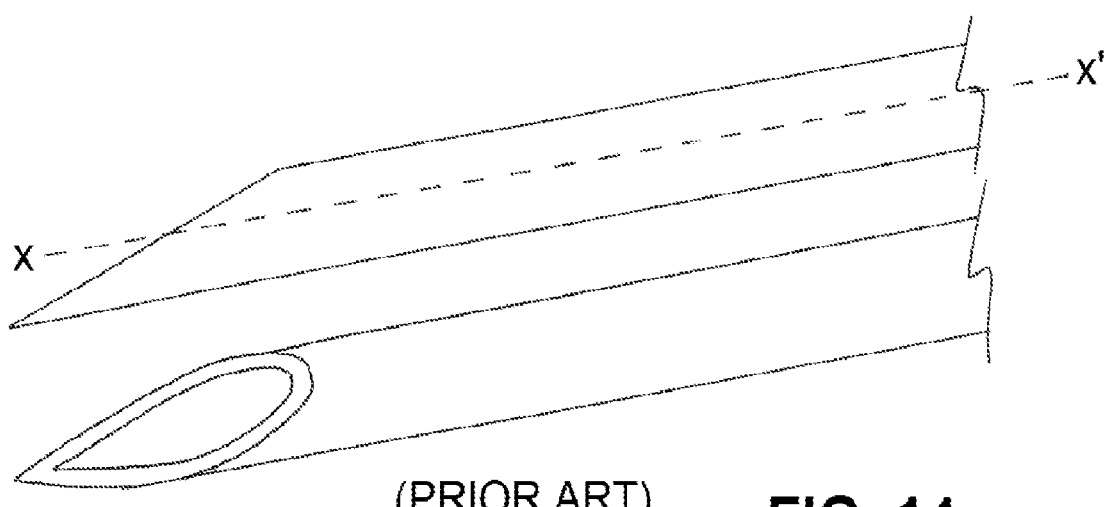
(PRIOR ART) FIG. 14

MATERIALS AND METHODS OF USING THE SAME TO IMPROVE STRUCTURAL INTEGRITY OF A WALL OF A MAMMALIAN LUMINAL ORGAN

PRIORITY AND INCORPORATION BY REFERENCE

The present application is related to, claims the priority benefit of, and is a U.S. 35 U.S.C. 371 national stage patent application of, International Patent Application Serial No. PCT/US2016/029893, filed Apr. 28, 2016, which is related to, and claims the priority benefit of, a) U.S. Provisional Patent Application Ser. No. 62/153,788, filed Apr. 28, 2015 b) U.S. Provisional Patent Application Ser. No. 62/293,187, filed Feb. 9, 2016, and c) U.S. Provisional Patent Application Ser. No. 62/312,642, filed Mar. 24, 2016, the contents of which are hereby incorporated by reference in their entirety into this disclosure. The contents of U.S. Pat. No. 8,328,752 of Kassab et al., issued Dec. 11, 2012, are also hereby incorporated by reference in their entirety into this disclosure.

BACKGROUND

Over time, and due to various factors, walls of various mammalian luminal organs may become substantially, and potentially detrimentally, thin. In the case of aneurysms for example, a thin vessel wall causes the vessel to protrude due to pressure therein, whereby rupture of the aneurysm can be extremely harmful, if not fatal.

In view of the same, the use of materials, and methods to deliver the same, into a wall of a mammalian vessel to improve the structural integrity thereof, would be appreciated in the medical arts and marketplace.

BRIEF SUMMARY

The present disclosure includes disclosure of materials for introduction into a wall of a mammalian luminal organ so to improve the overall internal structural integrity of the same, reduce stress, and/or reduce or eliminate the risk of rupture. Said materials may comprise one or more non-degradable, non-inflammatory biopolymers including, but not limited to, one or more of alginate, polytetrafluoroethylene (PTFE), and an elastomer, such as, for example, silicone elastomer, polyurethane, butyl rubber, and ethylene-propylene rubber, for example.

The present disclosure also includes disclosure of methods for introducing materials into a wall of a mammalian luminal organ so to improve the overall internal structural integrity of the same, reduce stress, and/or reduce or eliminate the risk of rupture. Furthermore, the present disclosure includes disclosure of methods of medical treatment, comprising the introduction of a quantity of a material into a wall of a mammalian luminal organ. Said methods of medical treatment may comprise the introduction of one or more quantities of one or more materials into a wall of a mammalian luminal organ.

The present disclosure includes disclosure of treating a patient having an aneurysm, comprising the introduction of one or more quantities of one or more materials into a wall of a blood vessel at the aneurysm. The present disclosure also includes disclosure of treating a patient having a thin bladder wall, comprising the introduction of one or more quantities of one or more materials into the thin bladder wall. In addition, the present disclosure includes disclosure of treating a patient having a thin esophageal wall, comprising the introduction of one or more quantities of one or more materials into the thin esophageal wall.

The present disclosure further includes disclosure of delivery mechanisms for delivering a material into a wall of a mammalian luminal organ.

In an exemplary embodiment of a system of the present disclosure, the system comprises one or more of the following: an engagement catheter, a skirt or suction cup, a delivery catheter, a needle, and/or a wire, as described and shown herein. Said systems, in various embodiments, are configured to deliver a liquid material, such as alginate, to a tissue of interest, such as cardiac tissue, to treat heart failure.

The present disclosure includes disclosure of a method for reinforcing a wall of a luminal organ, comprising the steps of inserting at least part of a needle into a blood vessel of a patient, advancing a distal end of the needle within the blood vessel to a location adjacent to a wall of a luminal organ of interest, piercing the wall of the luminal organ using the needle so that a tip of the needle is present within the wall of the luminal organ, injecting a substance through the needle and out of a distal portion of the needle so that at least some of the substance is present outside of the needle and inside of the wall of the luminal organ to reinforce the wall of the luminal organ, and withdrawing the distal portion of the needle from the wall of the luminal organ.

The present disclosure includes disclosure of a method for reinforcing a wall of a luminal organ, wherein the step of inserting is preceded by the steps of inserting a guidewire into the blood vessel, advancing a distal end of the guide wire within the blood vessel, advancing at least part of an engagement catheter over the guidewire and into the blood vessel, wherein the step of inserting is performed by inserting the at least part of the needle into the at least part of the engagement catheter which is then present within the blood vessel of the patient.

The present disclosure includes disclosure of a method for reinforcing a wall of a luminal organ, wherein the step of injecting is performed to inject a substance selected from the group consisting of stem cells, a polymer, an elastomer, a drug/medicament, cells other than stem cells, and a solution.

The present disclosure includes disclosure of a method for reinforcing a wall of a luminal organ, wherein the step of advancing the at least part of the engagement catheter over the guidewire and into the blood vessel is performed so that a distal end of the engagement catheter contacts the wall of the luminal organ and further comprises the step of providing suction through a lumen of the engagement catheter so that the distal end of the engagement catheter suctionally engages the wall of the luminal organ.

The present disclosure includes disclosure of a method for reinforcing a wall of a luminal organ, wherein the step of injecting is performed while the suction is being provided through the lumen of the engagement catheter.

The present disclosure includes disclosure of a method for reinforcing a wall of a luminal organ, wherein the step of advancing the at least part of the engagement catheter over the guidewire and into the blood vessel is performed while a sheath is at least partially present around the engagement catheter.

The present disclosure includes disclosure of a method for reinforcing a wall of a luminal organ, wherein the engagement catheter comprises a suction cup at a distal end of the engagement catheter, and wherein movement of the sheath relative to the engagement catheter allows the suction cup to be exposed outside of the sheath so that the suction cup can expand.

The present disclosure includes disclosure of a method for reinforcing a wall of a luminal organ, wherein the step of advancing the at least part of the engagement catheter over the guidewire and into the blood vessel is performed so that the suction cup of the engagement catheter contacts the wall of the luminal organ and further comprises the step of providing suction through a lumen of the engagement catheter so that the suction cup of the engagement catheter suctionally engages the wall of the luminal organ.

The present disclosure includes disclosure of a method for reinforcing a wall of a luminal organ, wherein when performing the step of injecting the substance through the needle and out of the distal portion of the needle, and substance that is injected out of the distal portion of the needle and not into the wall of the luminal organ would be removed from the patient via suction through the lumen of the engagement catheter.

The present disclosure includes disclosure of a method for reinforcing a wall of a luminal organ, further comprising the step of removing any of the substance that may leak from the wall of the luminal organ after the distal portion of the needle is withdrawn from the wall of the luminal organ via suction through the lumen of the engagement catheter.

The present disclosure includes disclosure of a method for reinforcing a wall of a luminal organ, wherein the step of piercing the wall of the luminal organ is performed to pierce a wall of a myocardium, and wherein the step of injecting the substance through the needle and out of the distal portion of the needle is performed to inject the at least some of the substance into the wall of the myocardium.

The present disclosure includes disclosure of a method for reinforcing a wall of a luminal organ, wherein the needle has at least a first distal aperture and at least a second distal aperture defined within the needle at the distal portion along a relative sidewall of the needle, and wherein the step of injecting is performed to inject the at least some the substance through the needle and out of the first distal aperture and the second distal aperture.

The present disclosure includes disclosure of a method for reinforcing a wall of a luminal organ, wherein the needle has a first distal aperture defined within the needle at a distal tip of the needle along a relative sidewall of the needle, wherein the first distal aperture is relatively curved at a distal portion of the first distal aperture and tapers inward toward a distal portion of the first distal aperture, and wherein the step of injecting is performed to inject the at least some the substance through the needle and out of the first distal aperture.

The present disclosure includes disclosure of a method for reinforcing a wall of a luminal organ, wherein the needle has a curved distal portion and a first distal aperture defined within the needle along at least part of the curved distal portion, and wherein the step of injecting is performed to inject the at least some the substance through the needle and out of the first distal aperture in a direction other than a direction defined by an axis of a portion of the needle proximal to the curved distal portion.

The present disclosure includes disclosure of a method for reinforcing a wall of a luminal organ, comprising the steps of inserting at least part of a system into a blood vessel of a patient, the system comprising a needle positioned within a lumen of an engagement catheter having a suction cup at its distal end, advancing the at least part of the engagement catheter within the blood vessel so that the suction cup of the engagement catheter contacts a wall of the luminal organ, providing suction through a lumen of the engagement catheter so that the suction cup of the engagement catheter suctionally engages the wall of the luminal organ, piercing the wall of the luminal organ, while under suction through the lumen of the engagement catheter, using the needle so that a tip of the needle is present within the wall of the luminal organ, injecting a substance through the needle and out of a distal portion of the needle so that at least some of the substance is present outside of the needle and inside of the wall of the luminal organ to reinforce the wall of the luminal organ.

The present disclosure includes disclosure of a method for reinforcing a wall of a luminal organ, wherein the step of advancing the at least part of the engagement catheter is performed while a sheath is at least partially present around the engagement catheter, and wherein movement of the sheath relative to the engagement catheter allows the suction cup to be exposed outside of the sheath so that the suction cup can expand.

The present disclosure includes disclosure of a method for reinforcing a wall of a luminal organ, comprising the steps of inserting at least part of a system into a blood vessel of a patient, the system comprising a needle positioned within a lumen of an engagement catheter having a suction cup at its distal end, advancing the at least part of the engagement catheter within the blood vessel so that the suction cup of the engagement catheter contacts a wall of a myocardium, providing suction through a lumen of the engagement catheter so that the suction cup of the engagement catheter suctionally engages the wall of the myocardium, piercing the wall of the myocardium, while under suction through the lumen of the engagement catheter, using the needle so that a tip of the needle is present within the wall of the myocardium, injecting a first substance through the needle and out of a distal portion of the needle so that at least some of the first substance is present outside of the needle and inside of the wall of the myocardium to reinforce the wall of the myocardium to treat the patient. The present disclosure includes disclosure of a method for reinforcing a wall of a luminal organ, wherein the step of injecting is performed to inject a first substance selected from the group consisting of stem cells, a polymer, an elastomer, a drug/medicament, cells other than stem cells, and a solution. The present disclosure includes disclosure of a method for reinforcing a wall of a luminal organ, wherein the step of injecting is performed to inject alginate into the wall of the myocardium. The present disclosure includes disclosure of a method for reinforcing a wall of a luminal organ, wherein the method further comprises the step of injecting a first substance through the needle and out of a distal portion of the needle so that at least some of the first substance is present outside of the needle and inside of the wall of the myocardium. The present disclosure includes disclosure of a method for reinforcing a wall of a luminal organ, wherein the step of injecting a second substance is performed to inject saline into the wall of the myocardium. The present disclosure includes disclosure of a method for reinforcing a wall of a luminal organ, wherein the step of injecting is performed to inject the substance having a first ionic content, and wherein the step of injecting the second substance is performed in inject the second substance having a second ionic content differing from the first ionic content.

BRIEF DESCRIPTION OF THE DRAWINGS

The disclosed embodiments and other features, advantages, and disclosures contained herein, and the matter of attaining them, will become apparent and the present disclosure will be better understood by reference to the following description of various exemplary embodiments of the present disclosure taken in conjunction with the accompanying drawings, wherein:

FIGS. 10, 11, 12, and 13 show perspective views of distal portion of needle, according to exemplary embodiments of the present disclosure;

FIG. 14 shows side and perspective views of prior art needles;

Figure 1:
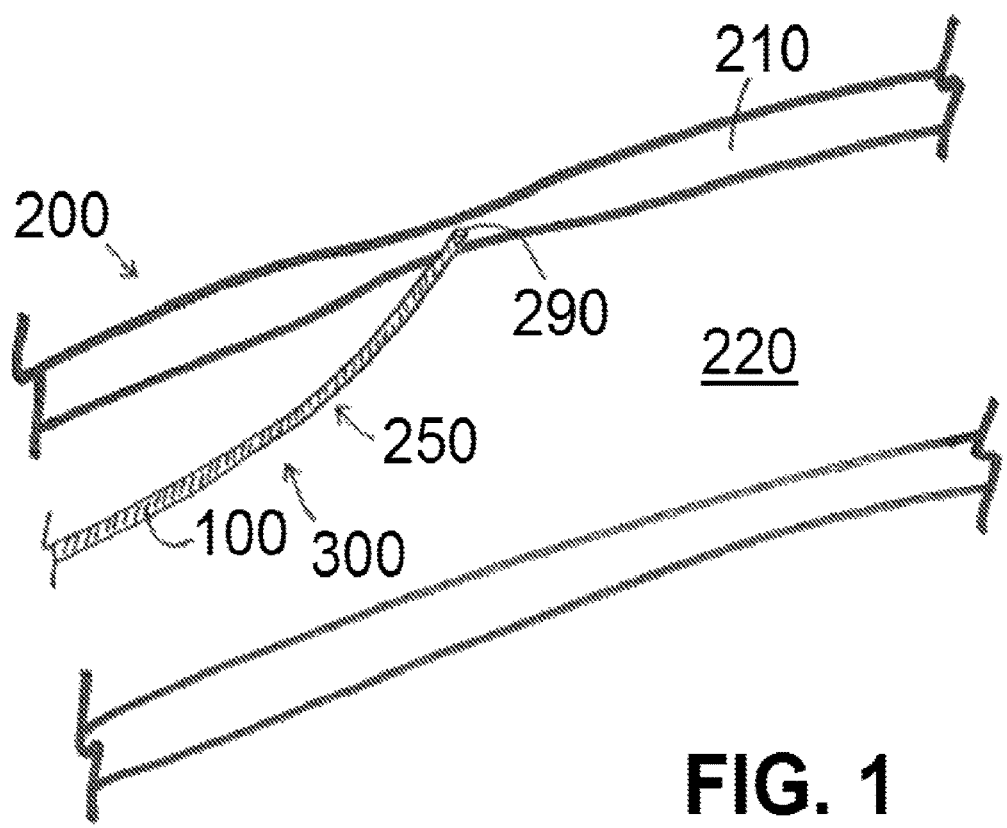
FIG. 1 shows a delivery mechanism delivering a material into a luminal organ wall via luminal or endothelial introduction/injection, according to an exemplary embodiment of the present disclosure.

An overview of the features, functions and/or configurations of the components depicted in the various figures will now be presented. It should be appreciated that not all of the features of the components of the figures are necessarily described. Some of these non-discussed features, such as various couplers, etc., as well as discussed features, are inherent from the figures themselves. Other non-discussed features may be inherent in component geometry and/or configuration.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

The present disclosure includes disclosure of various materials, and methods to administer the same, for injection into mammalian vessel or other luminal organ walls to provide additional support and/or integrity to the same.

In various embodiments of materials of the present disclosure, materials 100 or substances 1776 are non-degradable (or biodegradable, depending on application), non-inflammatory biopolymers. Exemplary materials 100 or substances 1776 within that scope included, but are not limited to, alginate, polytetrafluoroethylene (PTFE), elastomers (such as, for example, silicone elastomer, polyurethane, butyl rubber, and ethylene-propylene rubber, for example) and the like. Said materials 100 or substances 1776 are chosen so to provide a permanent or more permanent solution to the problems referenced herein, as said materials 100 or substances 1776 would last (not be biologically resorbed or otherwise broken down over time), would not introduce inflammation into the location of introduction, and are biocompatible. Additional materials 100 and/or substances 1776 of the present disclosure may include, but are not limited to, various drugs/medicaments, stem cells, other cells, etc., as used or developed in the art to treat a patient condition, for example. As said materials 100 or substances 1776 can be delivered via injection, as referenced in further detail herein, materials 100 or substances 1776 may be referred to as "liquid materials" in various embodiments, with the general understanding that said materials 100 would be injectable (such as a solution, a suspension, a gel, etc.), and may harden over time, as discussed in further detail herein.

Figure 2:
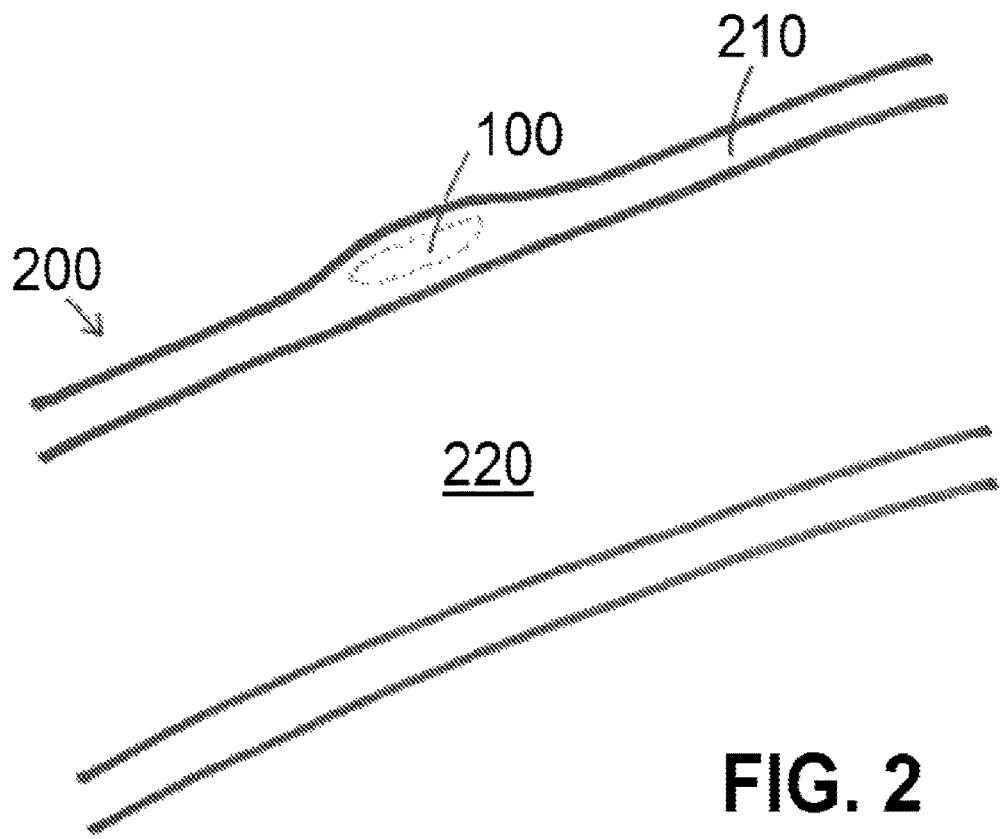
FIG. 2 shows material delivered into a luminal organ wall, according to an exemplary embodiment of the present disclosure.
Figure 3:
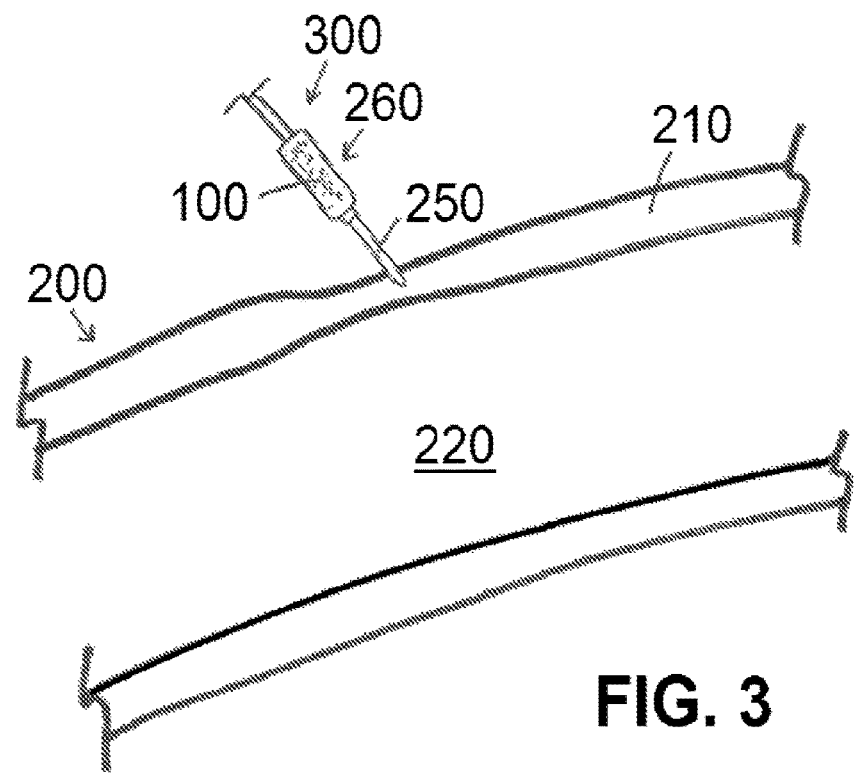
FIG. 3. shows a delivery mechanism delivering a material into a luminal organ wall via adventitial introduction/injection, according to an exemplary embodiment of the present disclosure.
Figure 4A:
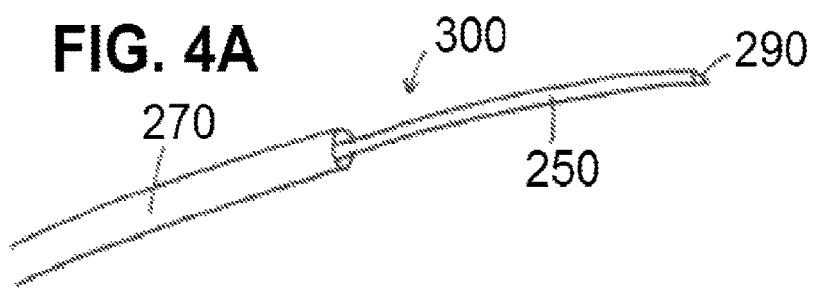
FIG. 4A shows a delivery mechanism configured as a needle within a catheter, according to an exemplary embodiment of the present disclosure.
Figure 4B:
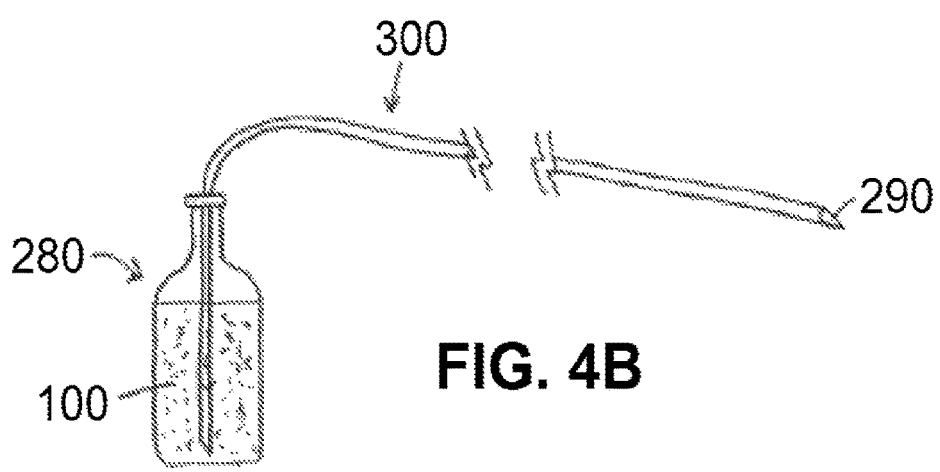
FIG. 4B shows a delivery mechanism configured as a needle in communication with a reservoir of material, according to an exemplary embodiment of the present disclosure.

Said materials 100 of the present disclosure can be introduced into a luminal organ wall 210 of a mammalian luminal organ 200, as shown in FIG. 2, so to, for example, increase a local and/or regional thickness of said luminal organ wall 210. Such an increase in thickness would then reduce luminal organ wall 210 stress, such as per LaPlace's law, so to prevent negative remodeling and/or potential rupture of luminal organ wall 210 at the location where materials 100 are introduced. In at least one embodiment/example, a first material 100, such as alginate and/or another polymeric material, can be positioned upon and/or injected into a mammalian luminal organ 200 or other non-luminal organ, as noted herein, and a second material 100, such as saline or another material 100 having a different ionic content than the first material 100, can subsequently be positioned upon and/or injected into a mammalian luminal organ 200 or other non-luminal organ. Such a procedure, for example, can be used to inject a liquid alginate (an exemplary material 100), and a second material 100, such as saline, can be injected so to cause the first material 100 to gel, harden, coagulate, etc., as may be desired, so to provide additional support upon and/or within mammalian luminal organ 200, such as by way of sodium ion exchange.

An exemplary introduction method of the present disclosure can be performed by way of injection, such as by using a needle 250 (alone, as part of a syringe 260, connected to or within a catheter 270, etc.) or other injection device known or developed in the medical arts to inject a material into a tissue. Such an injection can be made from within a lumen 220 of a mammalian luminal organ 200, referred to as luminal or endothelial introduction/injection, or from the outside of mammalian luminal organ 200, referred to as adventitial introduction/injection, by way of introducing material 100 from a material source 280 (which may be a reservoir containing material 100, such as a syringe 260 or other reservoir) through needle 250, out of needle aperture 290 (such as at a relative distal end of needle 250) into luminal organ wall 210. Various needles 250 or 1890, syringes 260, and/or catheters 270, etc., may be generally referred to herein as delivery mechanism(s) 300.

In various embodiments, for example, mammalian luminal organs 200 may comprise blood vessels, a thinned esophagus, a thin bladder, or another vessel or luminal organ within the mammalian body. In the case of a blood vessel as mammalian luminal organ 200, an aorta (relating to an aneurysm within a thin aorta wall), a thin cerebral vessel (relating to cerebral aneurysms), and the like, materials 100 of the present disclosure can be introduced into the luminal organ wall 210 of said mammalian luminal organs 200 so to improve the overall internal structural integrity of the same, reduce stress, and reduce or eliminate the risk of rupture, which can be fatal. In the case of a thin esophagus (achalasia) as mammalian luminal organ 200, such as in achalasia, materials 100 of the present disclosure can be introduced into the luminal organ wall 210 of said mammalian luminal organs 200 so to improve the overall internal structural integrity of the same, reduce stress, and improve the overall comfort level and health of the patient receiving the materials 100. The same can be said for a thin bladder as mammalian luminal organ 200, as materials 100, when introduced into luminal organ wall 210 of the same so to improve the structural integrity of the same. In view of the foregoing, various materials 100 of the present disclosure can be used to treat the aforementioned conditions/diseases.

Figure 5:
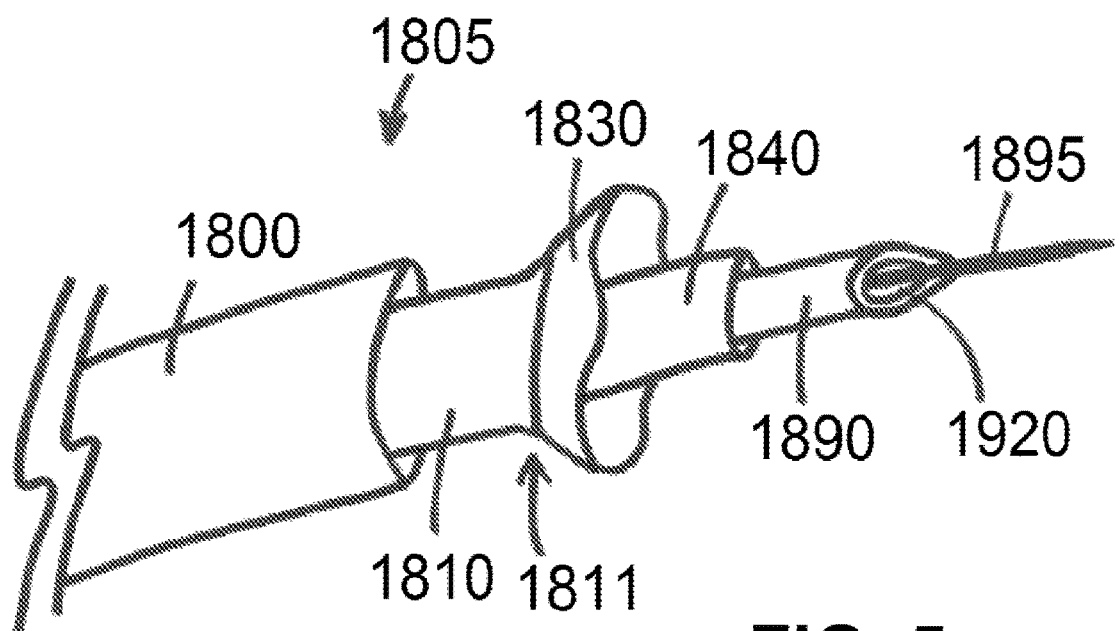
FIG. 5 shows a distal portion of system for isolating tissue and/or delivering a material, according to an exemplary embodiment of the present disclosure.

An exemplary system for isolating tissue and/or delivering a material 100 of the present disclosure is shown in FIG. 5. As shown in FIG. 5, distal portion of an exemplary system 1805 (which may also be referred to as a delivery mechanism 300) may comprise an engagement catheter 1810 having a skirt or suction cup 1830 at or near a distal end 1811 of engagement catheter 1810. System 1805 may further comprise a sleeve 1800 positioned around portions of engagement catheter 1810 and configured for sliding movement relative to engagement catheter 1810 such that movement of sleeve 1800 relative to engagement catheter 1810 can cause skirt or suction cup 1830 to be within or external to sleeve 1800. System 1805 may further comprise a delivery catheter 1840 (which may also be referred to as catheter 270) configured to fit within engagement catheter 1810 and configured for sliding movement relative to engagement catheter 1810. System 1805 may further comprise a needle 1890 (which may also be referred to as needle 250) defining a needle aperture 1920 (which may also be referred to as needle aperture 290) and configured to fit within delivery catheter 1840 and/or engagement catheter 1810 and configured for sliding movement relative to delivery catheter 1840 and/or engagement catheter 1810. System 1805 may further comprise a wire 1895 configured to fit within engagement catheter 1810, delivery catheter 1840, and/or needle 1890, and configured for sliding movement relative to engagement catheter 1810, delivery catheter 1840, and/or needle 1890. Components of such exemplary system 1805 embodiments may be as described within U.S. Pat. No. 8,328,752 of Kassab et al., the contents of which are expressly incorporated herein by reference.

Figure 6:
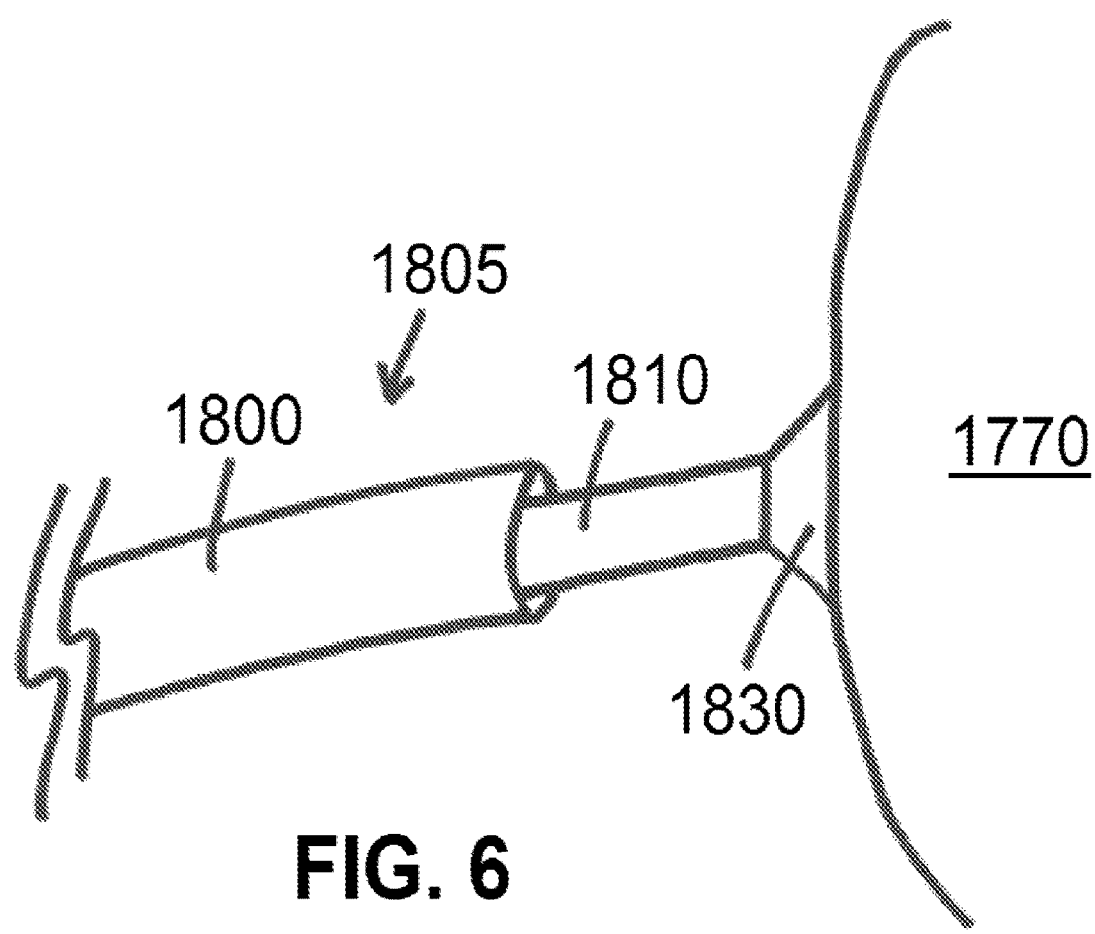
FIG. 6 shows a distal portion of a system suctionally affixed to a mammalian tissue, according to an exemplary embodiment of the present disclosure.

FIG. 6 shows a distal portion of an exemplary system 1805 of the present disclosure, with system 1805 comprising a sleeve 1800 positioned at least partially around engagement catheter 1810 having a skirt or suction cup 1830 at or near a distal end 1811 of engagement catheter 1810. Skirt or suction cup 1830 is shown as engaging cardiac tissue 1770, such as a myocardium, a left ventricle, or other portions of cardiac tissue 1770 or other mammalian tissue. Such engagement is provided via suction through engagement catheter 1810. Suction can be provided as described within U.S. Pat. No. 8,328,752 of Kassab et al., noting that various portions of devices and/or systems disclosed within U.S. Pat. No. 8,328,752 of Kassab et al. may be used in connection with devices and/or systems of the present disclosure.

Procedurally, portions of delivery mechanisms 300 and/or systems 1805 can be delivered subendocardially, such as by way of needle puncture, so that skirt or suction cup 1830 is ultimately positioned against cardiac tissue 1770 (or other mammalian tissues) as desired. Various delivery mechanisms 300 and/or portions of systems 1805 of the present disclosure can be delivered intravascularly, via thoracic puncture, etc., for ultimate use within the body, or can be used external to the body, such as upon the skin.

Figure 7:
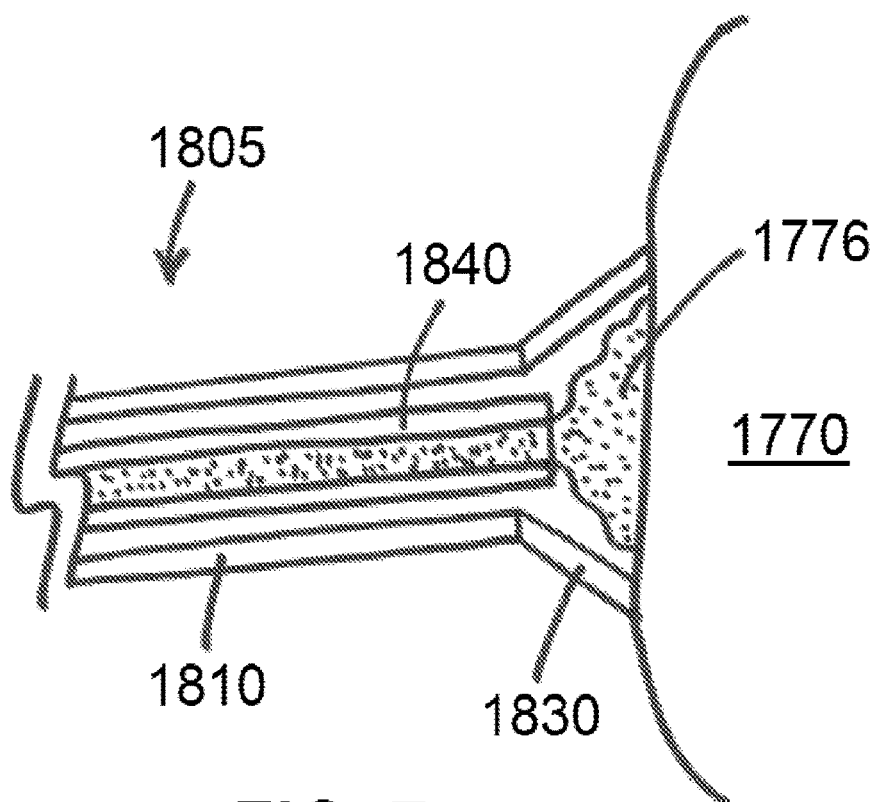
FIG. 7 shows a cut-away view of a distal portion of a system suctionally affixed to a mammalian tissue with a liquid material positioned therein, according to an exemplary embodiment of the present disclosure.
Figure 8:
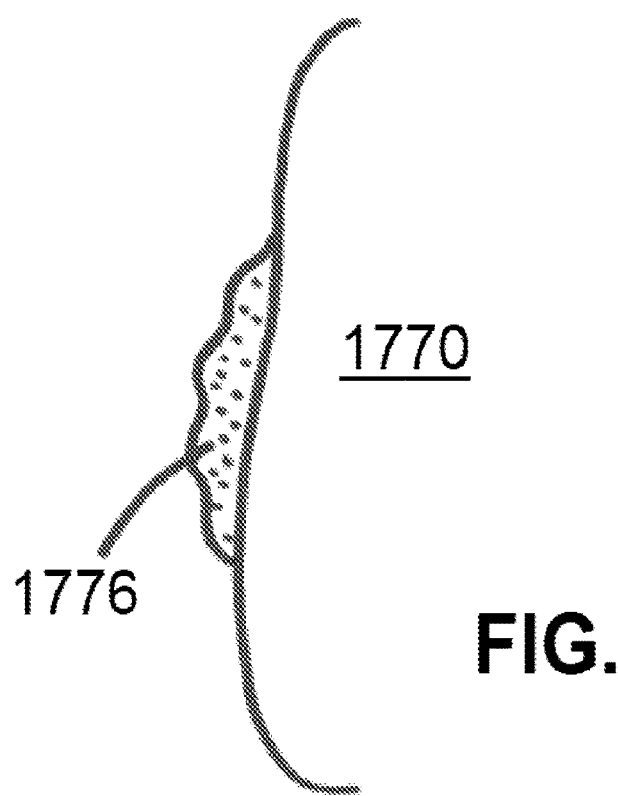
FIG. 8 shows a quantity of coagulated liquid material adhered to a mammalian tissue, according to an exemplary embodiment of the present disclosure.
Figure 9:
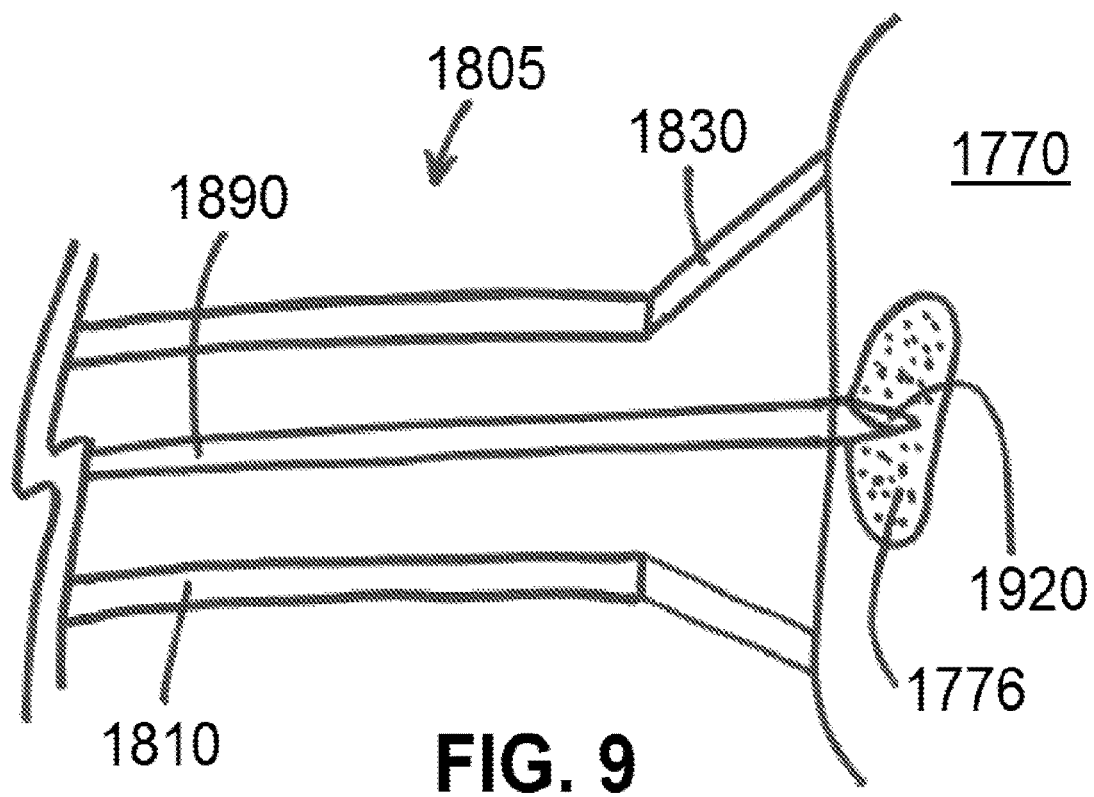
FIG. 9 shows a cut-away view of a distal portion of a system suctionally affixed to a mammalian tissue, according to an exemplary embodiment of the present disclosure.

FIG. 7 shows the injection of a substance 1776 (which can also be (or be referred to as) a material 100) through delivery catheter 1840 while skirt or suction cup 1830 of engagement catheter 1810 is suctionally engaged to cardiac tissue 1770. Substance 1776 can be injected through delivery catheter 1840, such as shown in FIG. 7, or delivered through needle 1890, such as shown in FIG. 9. Substance 1776 can congeal, coagulate, harden, and/or generally exist on a surface of a tissue (such as cardiac tissue 1770), such as shown in FIGS. 7 and 8, or within the tissue wall itself, such as shown in FIG. 9.

Figure 10:
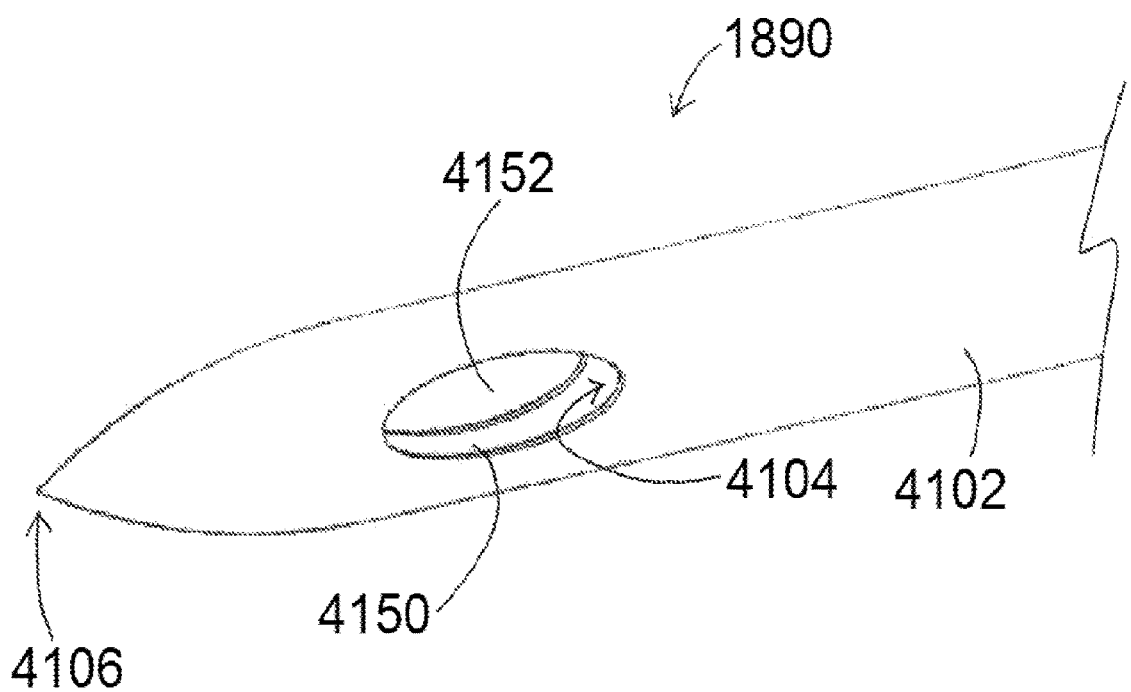

An exemplary embodiment of a portion of a needle of the present disclosure is shown in FIG. 10. As shown in FIG. 10, an exemplary needle 1890 (distal portion shown in the figure) comprises an elongated body 4102, which can be generally cylindrical in shape for at least part of an overall length of needle 1890, with elongated body 4102 defining a lumen 4104 extending along at least part of an overall length of needle 1890. Needle 1890, as shown in FIG. 10, terminates at a pointed tip 4106, with the size and shape of pointed tip 4106 permitting pointed tip 4106 to puncture a tissue or organ, such as the skin and/or a wall of a luminal organ, such as a heart wall.

Needle 1890, as shown in FIG. 10, has a first distal aperture 4150 and a second distal aperture 4152 defined therein near a distal portion of needle 1890 along a relative sidewall of elongated body 4102. First distal aperture 4150 and second distal aperture 4152 are defined within elongated body 4102 so that, for example, contents within lumen 4104 of needle 1890 can be injected out of needle 1890 via first distal aperture 4150 and/or second distal aperture 4152. First distal aperture 4150 and/or second distal aperture 4152 can each have various shapes, such as an oval shape (as shown in FIG. 10), a round shape, a square shape, and/or various other shapes. First distal aperture 4150 and second distal aperture 4152 may be defined within elongated body 4102 on opposite relative sides of elongated body 4102, such as shown in FIG. 10, or closer to one another (not directly opposite one another). As shown in FIG. 10, first distal aperture 4150 and second distal aperture 4152, in an exemplary embodiment, are not located at pointed tip 4106, but proximal to pointed tip 4106, so that first distal aperture 4150 and second distal aperture 4152 are along relative "sides" of elongated body 4102. Using such a needle 1890 embodiment, infusion of a material 100 or substance 1776 through said needle 1890 would be through the relative "side ports" (first distal aperture 4150 and second distal aperture 4152), noting that said side ports could be positioned at any location along a length of needle 1890, but having said side ports closest to pointed tip 4106 without impinging on needle 1890 curvature, for example, would reduce the required puncture depth, and therefore reduce the risk of potential perforation.

Figure 11:
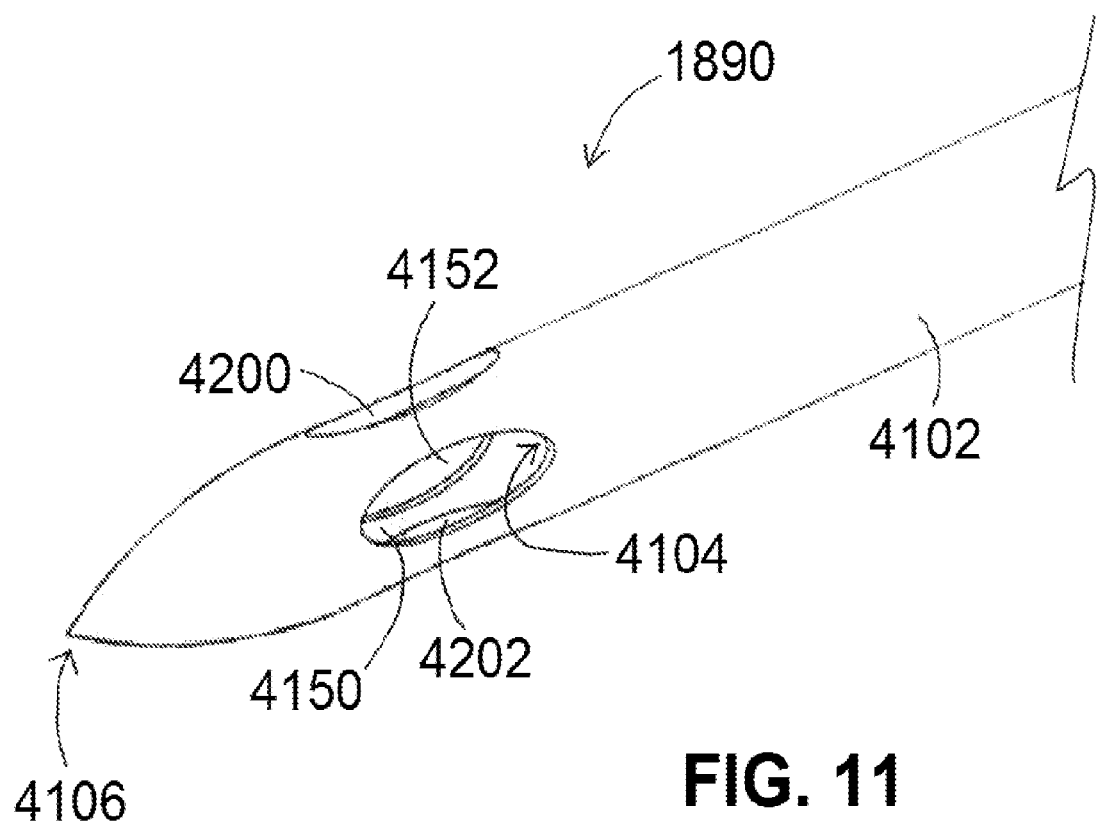

Another exemplary embodiment of a portion of a needle of the present disclosure is shown in FIG. 11. Needle 1890, as shown in FIG. 11, has a first distal aperture 4150, a second distal aperture 4152, a third distal aperture 4200, and a fourth distal aperture 4202 defined therein near a distal portion of needle 1890 along a relative sidewall of elongated body 4102. First distal aperture 4150, second distal aperture 4152, third distal aperture 4200, and fourth distal aperture 4202 are defined within elongated body 4102 so that, for example, contents within lumen 4104 of needle 1890 can be injected out of needle 1890 via first distal aperture 4150, second distal aperture 4152, third distal aperture 4200, and/or fourth distal aperture 4202. First distal aperture 4150, second distal aperture 4152, third distal aperture 4200, and fourth distal aperture 4202 can each have various shapes, such as an oval shape (as shown in FIG. 11), a round shape, a square shape, and/or various other shapes. First distal aperture 4150, second distal aperture 4152, third distal aperture 4200, and fourth distal aperture 4202 may be defined within elongated body 4102 so that they are equidistant from one another, such as shown in FIG. 11, or in a different arrangement, as may be desired. As shown in FIG. 11, first distal aperture 4150, second distal aperture 4152, third distal aperture 4200, and fourth distal aperture 4202, in an exemplary embodiment, are not located at pointed tip 4106, but proximal to pointed tip 4106, so that first distal aperture 4150, second distal aperture 4152, third distal aperture 4200, and fourth distal aperture 4202 are along relative "sides" of elongated body 4102. Such an embodiment would allow, for example, full radial infusion of material 100 or substance 1776 from needle 1890.

Various needle 1890 embodiments of the present disclosure can have various numbers of distal apertures (such as first distal aperture 4150, second distal aperture 4152, third distal aperture 4200, and/or fourth distal aperture 4202) defined along a relative sidewall of elongated body, such as two (as shown in FIG. 10), three, four (as shown in FIG. 11), five, or more distal apertures.

Figure 12:
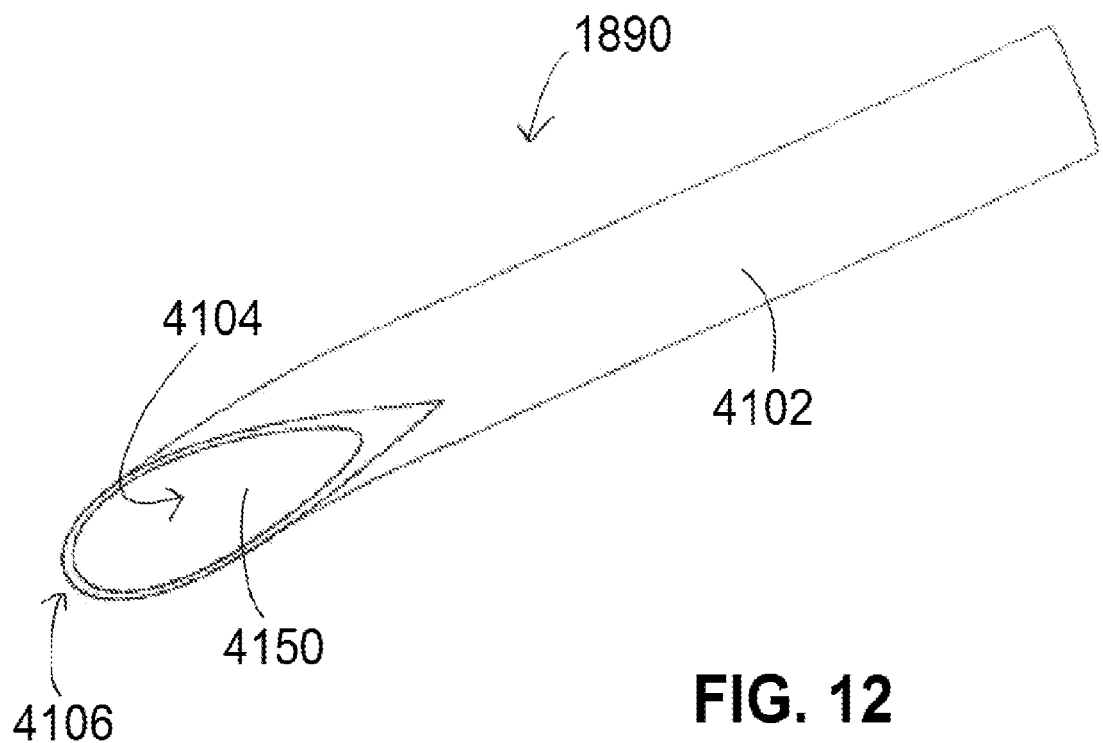

Another exemplary embodiment of a portion of a needle of the present disclosure is shown in FIGS. 12 and 13. Needle 1890, as shown in FIGS. 12 and 13, comprises an elongated body and a first distal aperture 4150 (which may also be referred to as needle aperture 1920, as referenced herein) defined within elongated body 4102 at pointed tip 4106 so that first distal aperture 4150 extends proximally from pointed tip 4106 at a distal end of needle 1890. First distal aperture 4150 can be relatively round and/or curved at a distal portion, and taper inward toward a proximal portion of first distal aperture 4150, such as shown in FIG. 12, for example. First distal aperture 4150, such as shown in FIG. 13, is "open" on a relative "side" of elongated body 4102, so that a substance present within lumen 4104 can exit first distal aperture 4150, such as when needle 1890 is used for injection, so that substance is directed out of needle 1890 in a direction that is not the direction of the axis defined by elongated body 4102, such as shown in FIG. 13 via X-X'. Such an embodiment would allow for orthogonal injection at a deepest point of insertion, as described in further detail herein.

Prior art needles, as shown in the side view and perspective views shown in FIG. 14 for example, generally include a distal aperture that is angled from one relative "side" of the needle to the other, such that the distal aperture is angled as shown in the upper part of said figure. Needle 1890 shown in FIGS. 12 and 13, for example, differ from the needles shown in FIG. 14 in that needles 1890 shown in FIGS. 12 and 13 define a first distal aperture 4150 having an opening that is generally parallel with the axis defined by elongated body 4102, such as shown in FIG. 13 via X-X'. Substances discharged from the distal aperture in the needle shown in FIG. 14 would be discharged in a direction defined by the axis shown via X-X' therein, while substances injected through any of needles 1890 shown in FIGS. 10-13 would not be discharged in a direction defined by the axis shown via X-X' in FIG. 13, as said substances would be discharged in a direction other than that defined by said axis.

Various needles 1890 of the present disclosure can be used alone, or in conjunction with other devices, to deliver a substance to a targeted tissue as may be desired. One such delivery process is the process of delivering a substance subendocardially along with suction, as follows.

Figure 15:
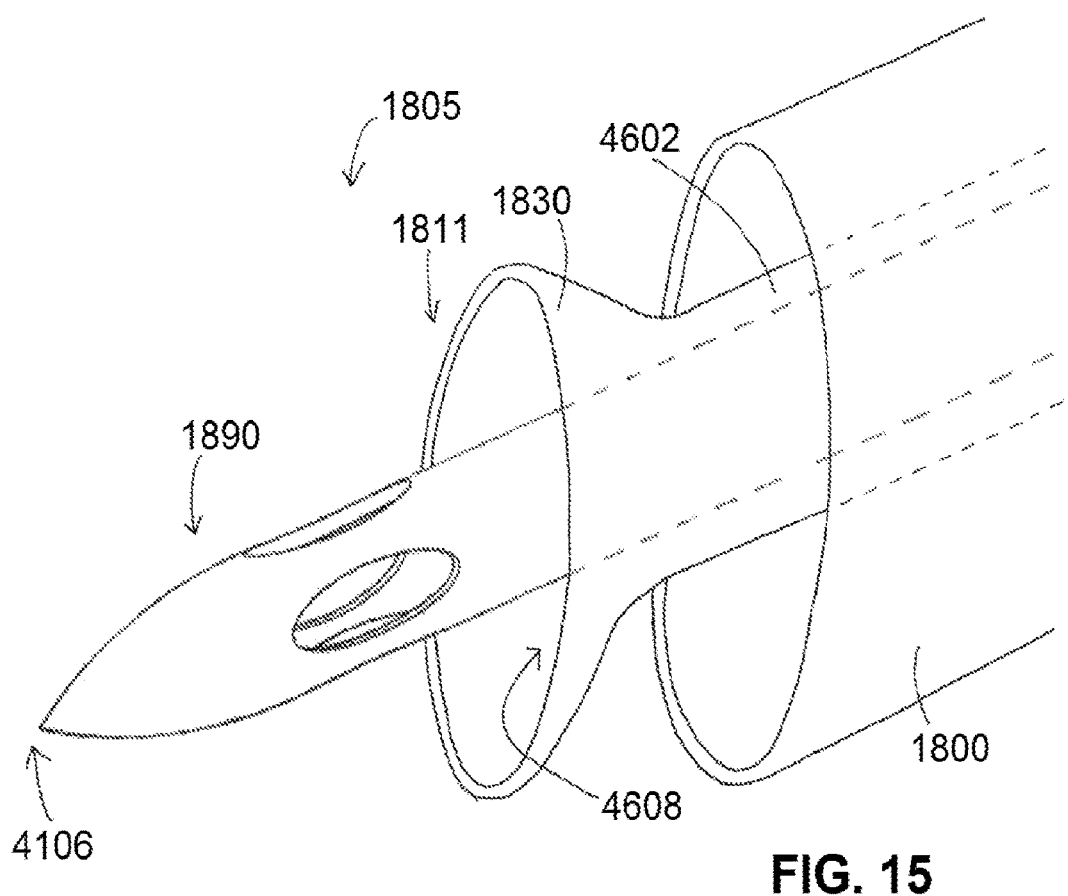
FIG. 15 shows a distal portion of system for isolating tissue and/or delivering a material, according to an exemplary embodiment of the present disclosure.

FIG. 15 shows portions of an exemplary system 1805 of the present disclosure. As shown in FIG. 15, an exemplary system 1805 of the present disclosure comprises a needle 1890 of the present disclosure and a suction catheter 4602 (which may also be referred to herein as an engagement catheter 1810) having a skirt or suction cup 1830 located at a distal end 1811 of suction catheter 4602. Needle 1890 can be delivered through a lumen 4608 defined within suction catheter 4602, such as shown in FIG. 15, and an optional sleeve 1800 can be positioned around at least part of suction catheter 4602. Procedurally, a guide wire (not shown) can be delivered through the skin, into an artery (such as the femoral artery or another artery of interest), and a distal end of the guide wire can be advanced intravascularly until it is positioned at a location of interest, such as inside a left ventricle of the heart. Needle 1890, catheter 4602, sleeve 1800, and/or a combination of two or more of the foregoing, can be advanced along the guidewire so that ultimately the distal end of needle 1890 and the distal end 1811 of suction catheter 4602 are positioned at or near a tissue of interest, such as the free wall (or the subendocardium or the subendocardial wall) of the left ventricle. Skirt or suction cup 1830 can be positioned against the tissue of interest, and suction through suction catheter 4602 can cause skirt or suction cup 1830 to suctionally adhere to said tissue. Pointed tip 4106 of needle 1890 can be advanced into the tissue of interest before suction is applied via suction catheter 4602, at the same time suction is started through suction catheter 4602, or after suction is started through suction catheter 4602, as may be desired. After the various distal apertures (such as distal apertures 4150, 4152, 4200, and/or 4202, for example) are located within the tissue of interest or are located within a luminal organ of interest, a substance can be delivered through lumen 4104 of needle and out of said apertures 4150, 4152, 4200, and/or 4202, for example. In at least one embodiment, needle 1890 is advanced into a free wall of a left ventricle of a heart so that apertures 4150, 4152, 4200, and/or 4202, for example are located within said free wall, and a substance, such as a substance used to strengthen a tissue wall, is injected into the tissue wall. Skirt or suction cup 1830, at a distal end of suction catheter 4602, has a larger distal perimeter or circumference than the perimeter or circumference of the remainder of suction catheter 4602 (or at least the elongated portion of suction catheter 4602) so to allow for a larger suction area against the tissue or organ of interest.

Delivery mechanisms 300 and/or systems 1805 can be used as follows, by way of example:

a) to suctionally engage a mammalian tissue or organ so to stabilize said tissue or organ; and/or b) to suctionally engage a tissue or organ so to directly deliver a medicament, such as a pharmaceutical compound (a drug), an injectable material (such as a biopolymer), a lead, cells, a coil, and/or another medical device; and/or c) to suctionally engage a tissue or organ so to facilitate delivery of a delivery catheter 1840, a needle 1895, and/or a wire 1920 through delivery mechanism 300, whereby said delivery catheter 1840 and/or needle 1895 can be used to deliver a medicament, such as a pharmaceutical compound, an injectable material, a lead, a coil, and/or another medical device, and/or whereby wire 1920 can be used to guide portions of delivery mechanism 300 and/or system 1805 within the body.

Figure 16:
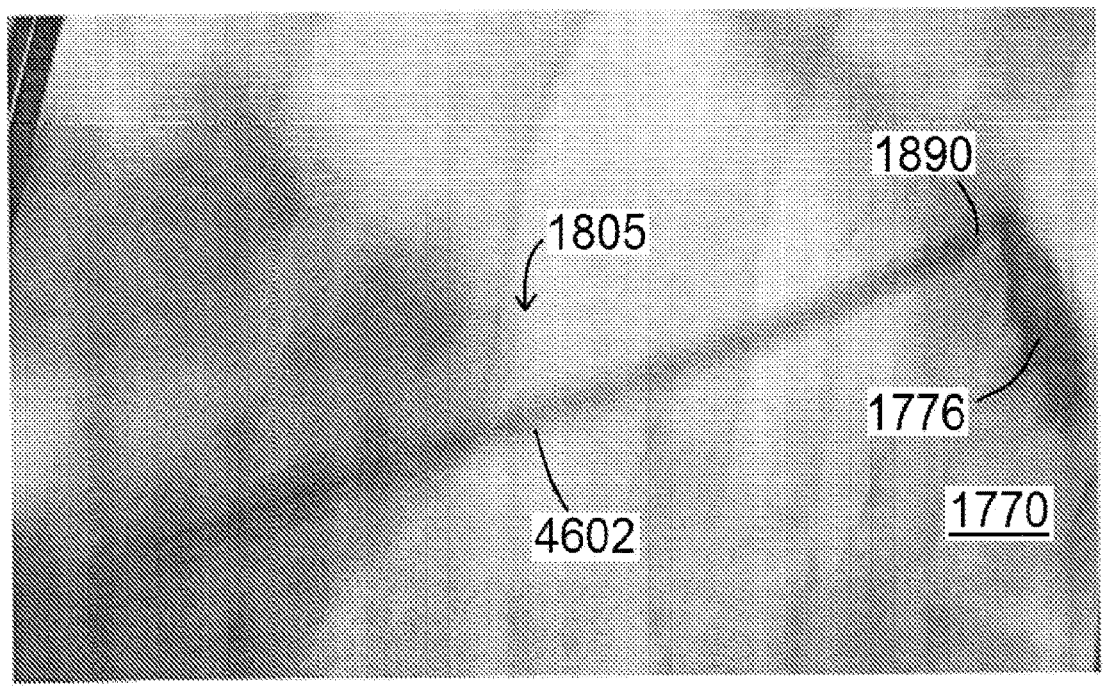
FIG. 16 shows a photograph of injection of a substance using a needle while under suction via a suction catheter, according to an exemplary embodiment of the present disclosure.
Figure 17:
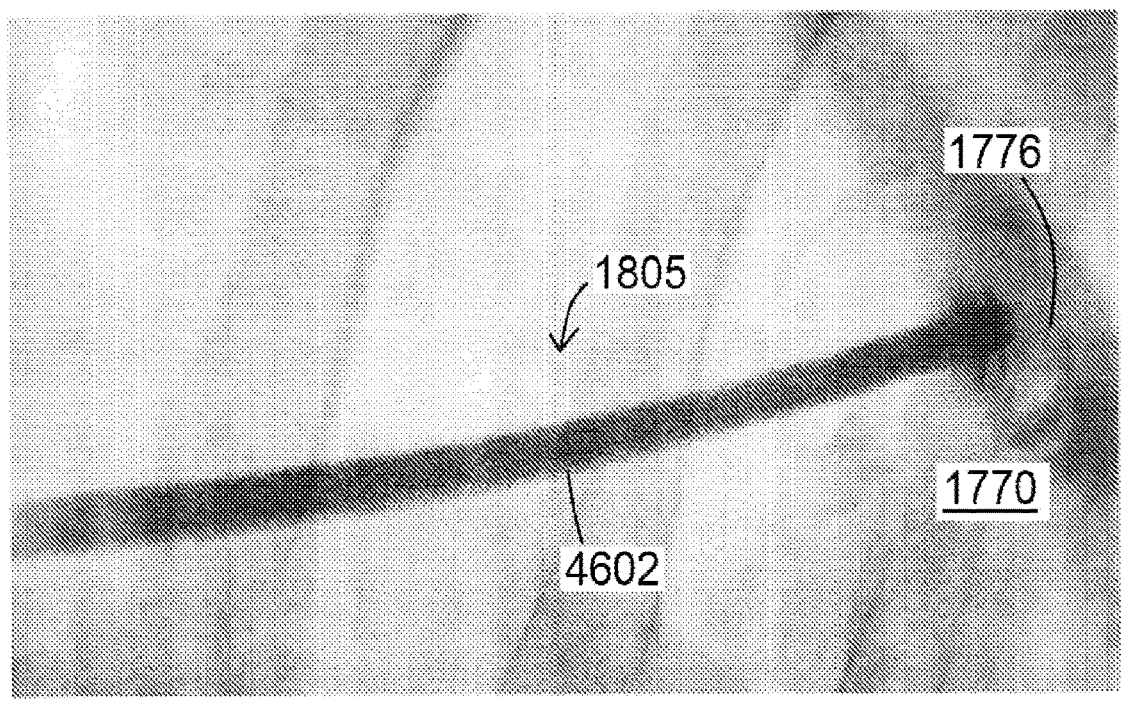
FIG. 17 shows a photograph of a suction catheter suctionally engaging a tissue after injection of the substance, according to an exemplary embodiment of the present disclosure.
Figure 18:
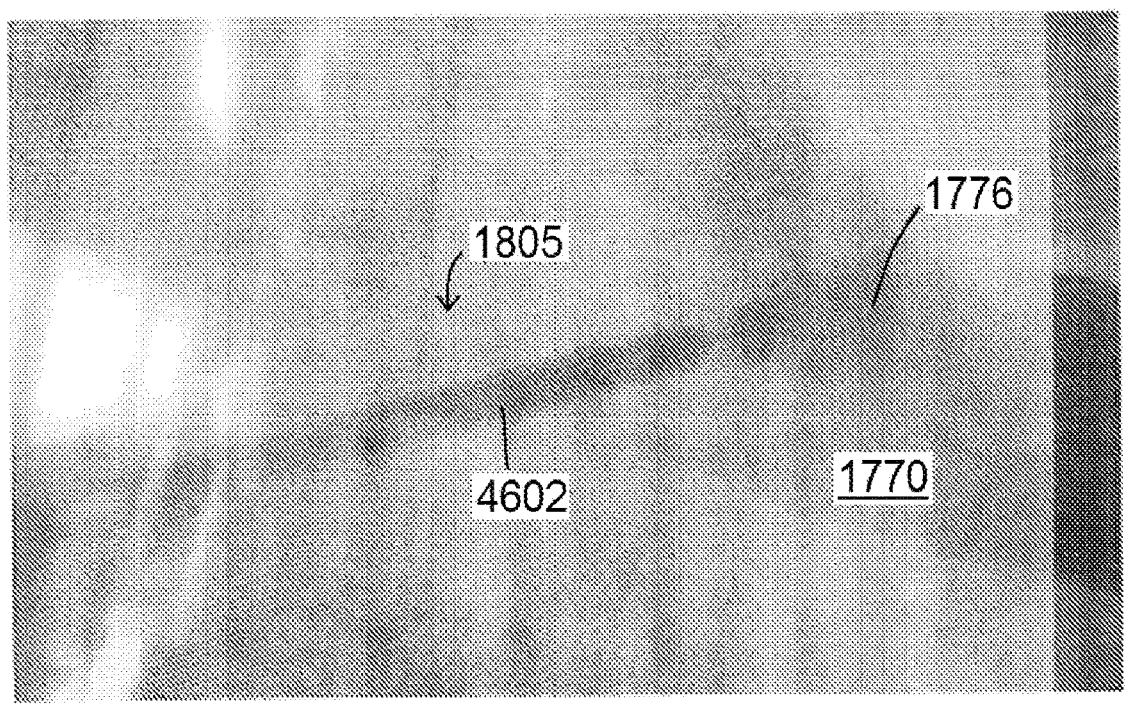
FIG. 18 shows a photograph of a suction catheter disengaged from a tissue after injection of the substance, according to an exemplary embodiment of the present disclosure.

In at least one embodiment of using a delivery mechanism and/or system 1805 of the present disclosure, said delivery mechanism 300 and/or system 1805 is used as follows, noting that all steps are not required, but may be performed:

i) after puncturing the skin to provide access to an artery of interest, advancing a wire 1895 so that a distal end of wire 1895 is positioned at a desired location within the body, such as within a left ventricle of a heart, by way of the femoral artery to the aorta to the left ventricle, for example;

ii) advancing other portions of delivery mechanisms 300 and/or systems 1805 over said wire 1895, such as an engagement catheter 1810 or suction catheter 4602, needle 1890, sleeve 1800, etc, so that distal portions of each are located at, near, or within the left ventricle of the heart;

iii) applying suction through engagement catheter 1810 or suction catheter 4602 so that skirt or suction cup 1830 of engagement catheter 1810 or suction catheter 4602 can suctionally engage a tissue of interest, such as the free wall of the left ventricle;

iv) inserting a distal end of needle 1890 into the tissue of interest, such as the free wall of the left ventricle, and injecting a material 100 or substance 1776 into said tissue (such as into the free wall of the left ventricle), such as to inject a biopolymer into the free wall itself to support the free wall, all while suction is applied through engagement catheter 1810 or suction catheter 4602, such as shown in FIG. 16, for example;

v) withdrawing needle 1890 from said tissue, while suction is applied through engagement catheter 1810 or suction catheter 4602, so that any material 100 or substance 1776 that may leak from the needle puncture location of said tissue would be removed from the left ventricle via suction through engagement catheter 1810 or suction catheter 4602, such as shown in FIG. 17, for example; and vi) after a desired amount of time has elapsed, ceasing suction through engagement catheter 1810 or suction 4602 so to disengage from the tissue of interest, such as cardiac tissue 1770, such as shown in FIG. 18, for example.

Needle 1890 design, such as shown in FIGS. 10-13 and referenced herein, allows for material 100 or substance 1776 to be injected at an angle other than 0° relative to the elongated axis of needle 1890, as referenced herein. Such a relative sideways or angled injection may allow material 100 and/or substance 1776 to better remain within the tissue of interest and potentially reduce the leakage from the tissue of interest when needle 1890 is removed therefrom.

Re: step iv) above, needle 1890 may be positioned within the tissue for a desired period of time, such as one minute, two minutes, or longer or shorter as may be desired, to allow material 100 or substance 1776 to harden, congeal, etc., and therefore reduce potential leakage from said tissue. One notable risk of leakage is the potential embolization of said material 100 or substance 1776, which could be fatal (potentially) should it be released within the bloodstream. Such a method, by way of using suction during and after the injection procedure, would remove any potential leaked material 100 or substance 1776 from the bloodstream.

Said methods, for example, could be performed to treat a cardiac condition of a patient, such as a patient with a weakened left ventricle wall, by supporting/strengthening said left ventricle wall using an injected biopolymer. Such a treatment would be performed endovascularly instead of requiring open chest surgery, for example, resulting in less trauma to the patient, a lower infection risk, and likely less cost to perform the procedure.

Figure 19:
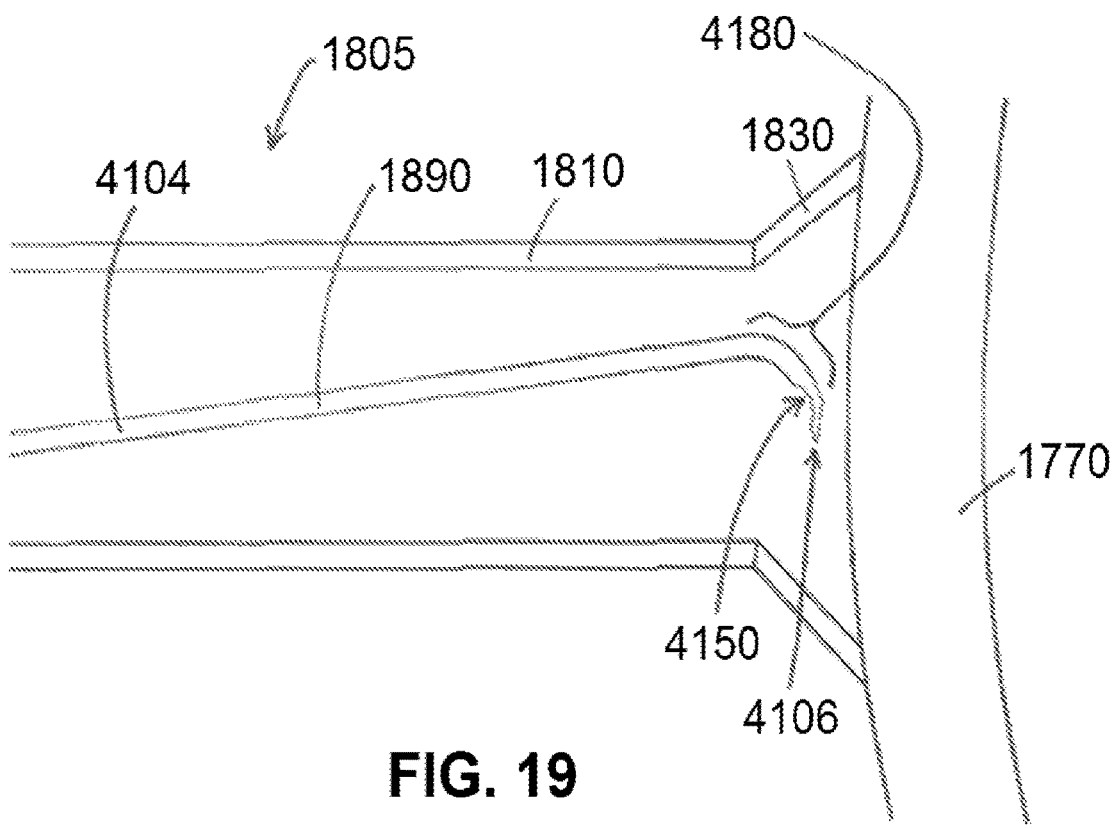
FIG. 19 shows a cut-away view of a distal portion of a system suctionally affixed to a mammalian tissue via an engagement catheter, according to an exemplary embodiment of the present disclosure.

FIGS. 19-24 show an embodiment of devices and systems used to perform such a method. For example, FIG. 19 shows a distal portion of an exemplary system 1085 comprising at least an engagement catheter 1810 having a skirt or suction cup 1830 at its distal end, and a needle 4150 having a curved distal portion 4180, in an exemplary embodiment. Suction can be applied through engagement catheter 1810, as shown in FIGS. 19-24, so to suctionally attach skirt or suction cup 1830 to cardiac tissue 1770 or other mammalian tissue.

Figure 20:
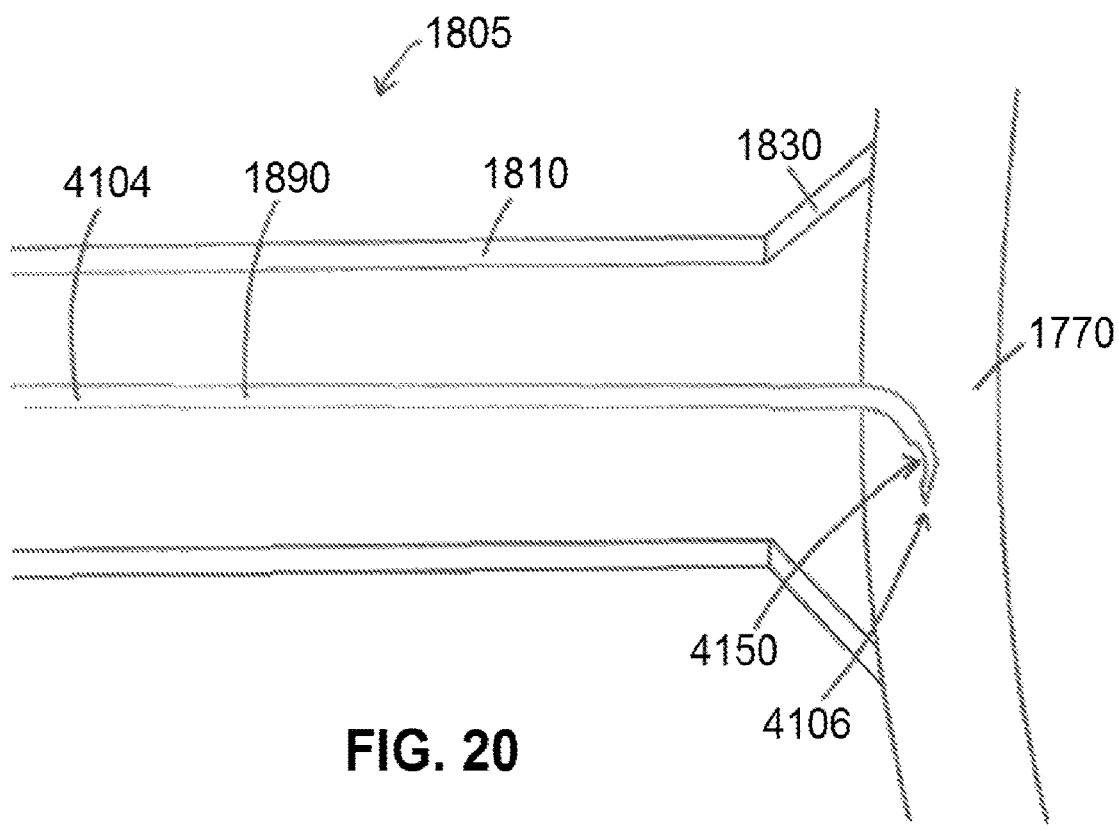
FIG. 20 shows a cut-away view of a distal portion of a system suctionally affixed to a mammalian tissue and whereby a needle has punctured a tissue of interest, according to an exemplary embodiment of the present disclosure.
Figure 21:
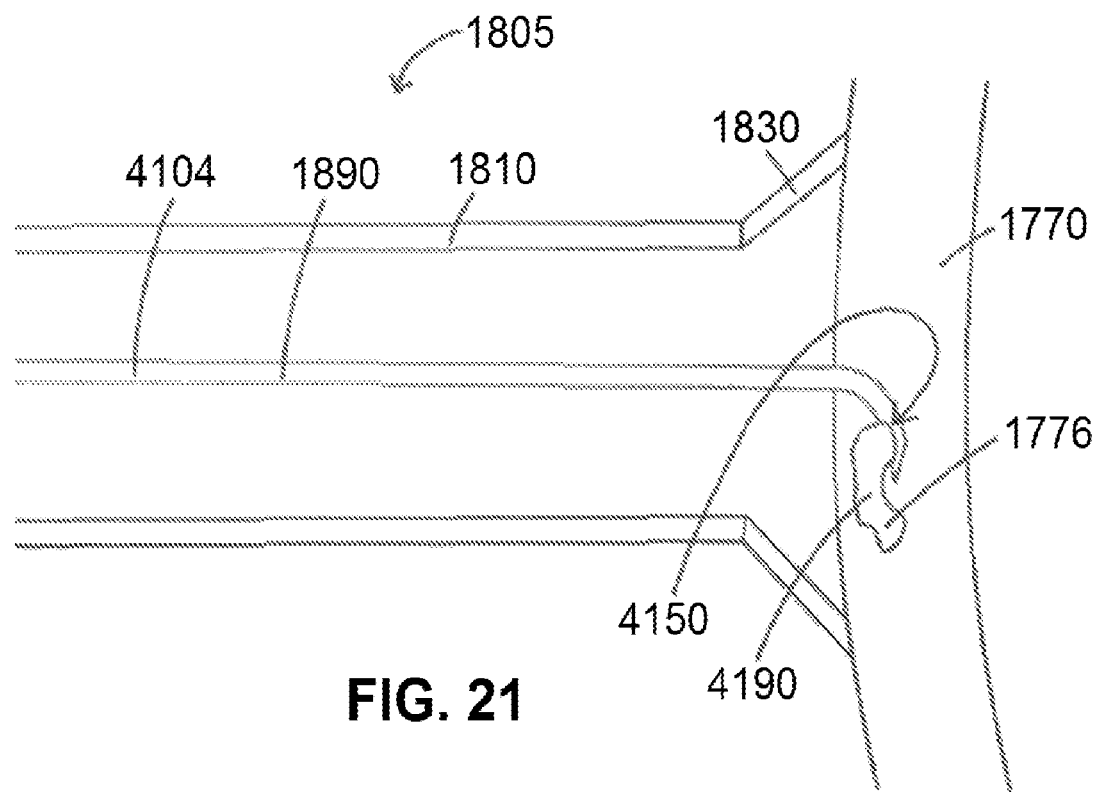
FIG. 21 shows a cut-away view of a distal portion of a system suctionally affixed to a mammalian tissue and whereby a needle has injected a bolus of a substance into the tissue of interest, according to an exemplary embodiment of the present disclosure.

FIG. 20 shows needle 1890, whereby pointed tip 4106 of needle 1890 was used to puncture tissue 1770. FIG. 21 shows needle 1890 being used to inject a substance 1776, through lumen 4104 of needle 1890 and out of first distal aperture 4150 (and/or any other distal apertures of the present disclosure) into tissue 1776, forming a bolus 4190 of substance 1776 within tissue. Such an injection can also be performed while under suction within engagement catheter 1890.

In various embodiments, such as shown in FIGS. 19-22, first distal aperture 4150 (and/or any other distal apertures of the present disclosure) are relatively elongated, such as comprising a general oval or ovular shape, for example, so to generate a bolus 4190 having a geometry that is less likely to leak out of tissue 1770 upon removal of needle 1890 therefrom. Due to one or more characteristics of needle 1890, such as, for example, an elongated first distal aperture aperture 4150 (and/or any other distal apertures of the present disclosure), and/or a plurality of distal apertures as referenced herein, and/or a curved distal portion 4180 of needle 1890, for example, a bolus 4190 of substance 1770 is less likely to leak from tissue 1770 upon removal of needle 1890 therefrom as compared to using a prior art needle, as there would be a direct/straight path for potential bolus 4190 leakage using a prior art needle as compared to needles 1890 of the present disclosure.

Figure 22:
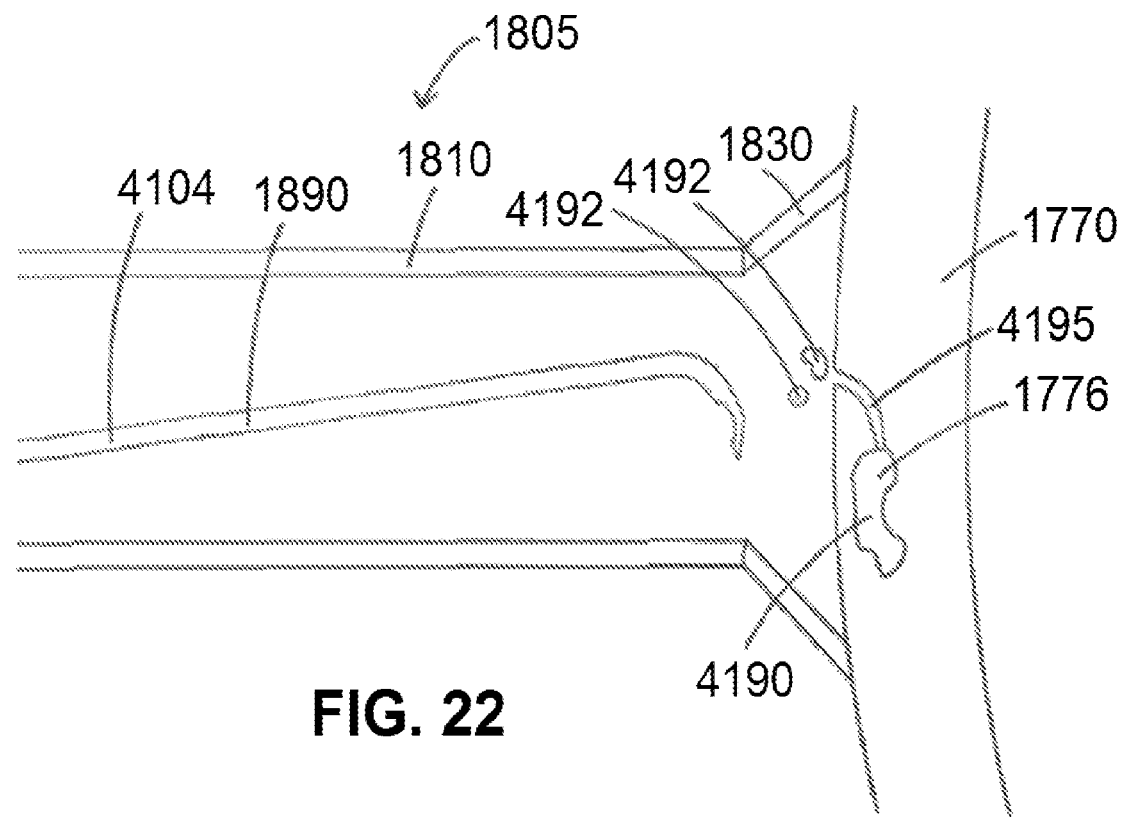
FIG. 22 shows a cut-away view of a distal portion of a system suctionally affixed to a mammalian tissue and after the needle has injected a bolus of a substance into the tissue of interest, according to an exemplary embodiment of the present disclosure.
Figure 23:
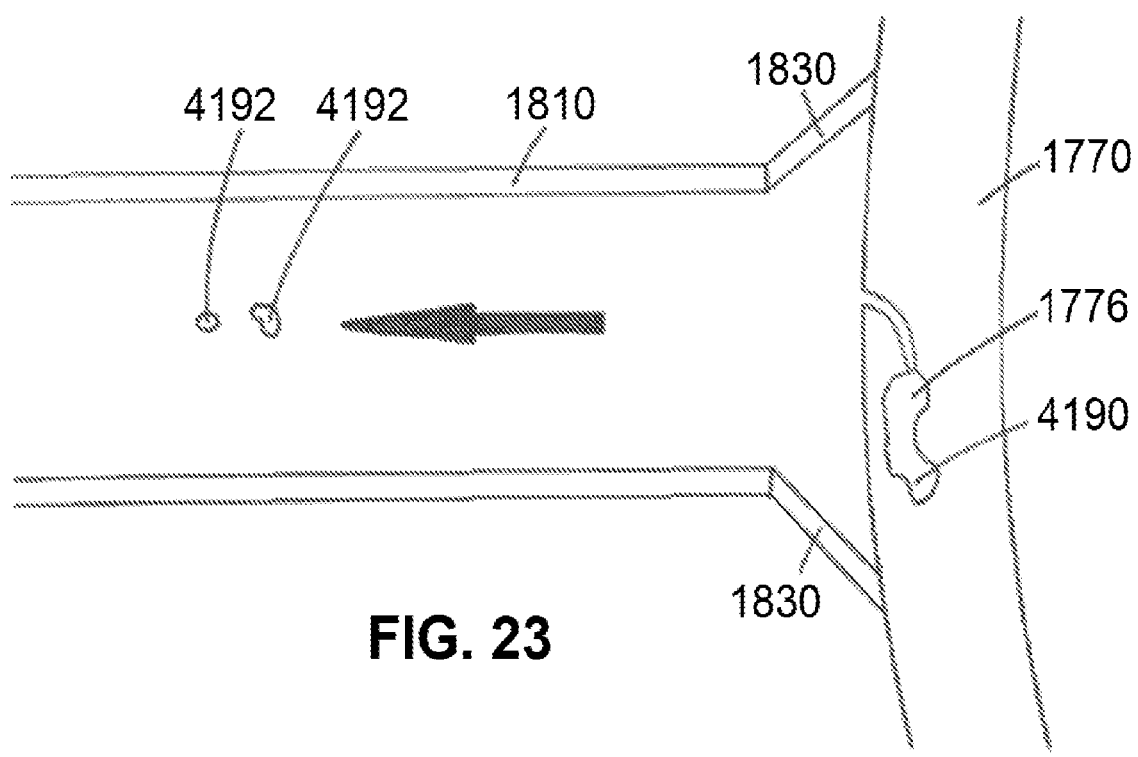
FIG. 23 shows a cut-away view of a distal portion of a system suctionally affixed to a mammalian tissue and used to remove escaped substance using suction within the engagement catheter, according to an exemplary embodiment of the present disclosure.
Figure 24:
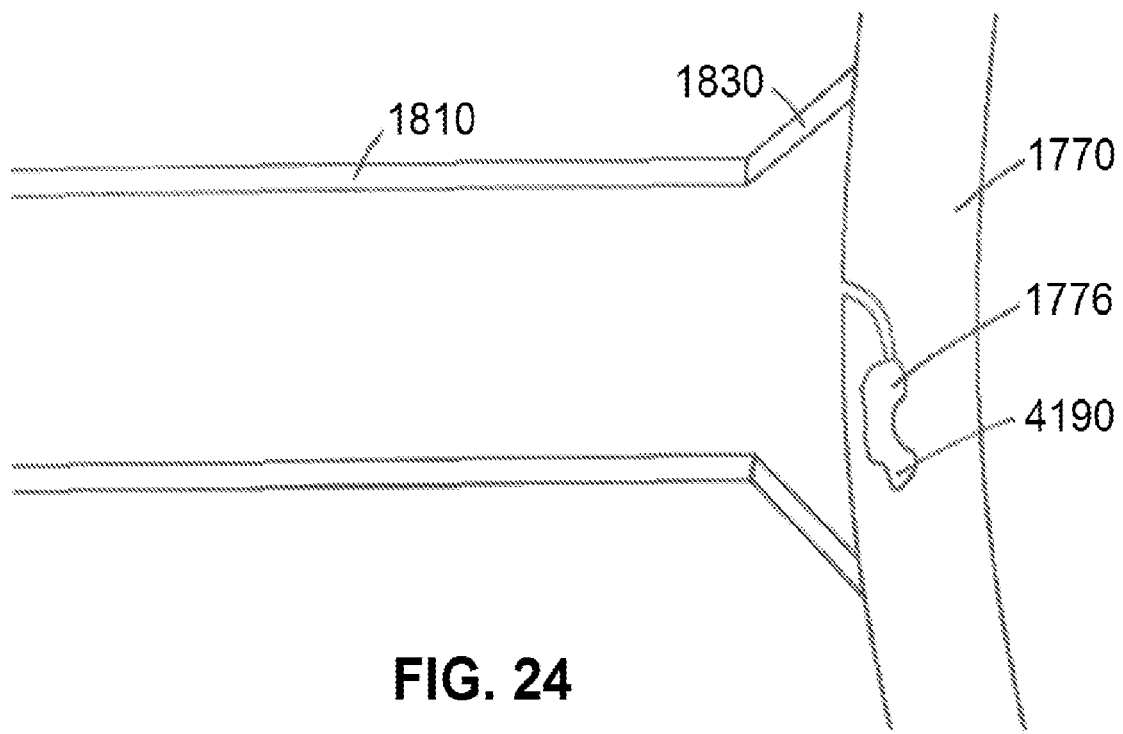
FIG. 24 shows a cut-away view of a distal portion of a system and no escaped substance, according to an exemplary embodiment of the present disclosure.

However, and even using a needle 1890 of the present disclosure to inject a bolus 4190 of substance 1776 into a tissue 1770, leakage of said substance 1776 may still occur, such as shown in FIG. 22, whereby escaped substance 4192 may have leaked out of tissue 1770 via puncture aperture 4195 upon or after withdrawal of needle 1890 from tissue 1770. However, and using an exemplary system 1805 of the present disclosure, suction through engagement catheter 1810 causes escaped substance 4192 to be withdrawn from the person through engagement catheter 1810, such as shown in FIG. 23, in the general direction of the arrow shown therein. Such a use of engagement catheter 1810 allows escaped substance 4192 to be safely withdrawn from the person versus potentially allowing said escaped substance 4192 to enter the bloodstream, for example, and potentially cause an embolus and/or generally cause escaped substance 4192 to enter an area of the body where escaped substance 4192 is not intended to be.

Suction can be applied as long as desired, such as for a duration whereby the user of system 1805 is comfortable that no additional substance 1776 will leak out of tissue 1770, such as whereby closure or relative closure of puncture aperture 4195 can occur, and/or whereby substance 1776 has an opportunity to congeal, coagulate, harden, etc. In such a situation, suction can cease, such as indicated within FIG. 24, whereby no escaped substance 4192 exists and bolus 4190 of substance 1776 remains within tissue 1770 as desired. Engagement catheter 1805 can then be safely withdrawn from the body, for example.

Systems 1805, such as referenced herein, can provide a user of said system(s) 1805 with the certainty that the substance 1776 delivered to the tissue 1770 of interest, such as, for example, to ensure that stem cells (an exemplary substance 1776) is delivered to a myocardium (an exemplary tissue 1770), so that substance 1776 can treat the patient as desired.

Other uses of exemplary delivery mechanisms 300 and/or systems 1805 are also contemplated herein and within the present disclosure, such as during known or developed medical procedures whereby suction engagement of a catheter to a tissue or organ 5600 is part of the procedure.

While various materials and methods of using the same have been described in considerable detail herein, the embodiments are merely offered as non-limiting examples of the disclosure described herein. It will therefore be understood that various changes and modifications may be made, and equivalents may be substituted for elements thereof, without departing from the scope of the present disclosure. The present disclosure is not intended to be exhaustive or limiting with respect to the content thereof.

Further, in describing representative embodiments, the present disclosure may have presented a method and/or a process as a particular sequence of steps. However, to the extent that the method or process does not rely on the particular order of steps set forth therein, the method or process should not be limited to the particular sequence of steps described, as other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A method for reinforcing a wall of a luminal organ, comprising the steps of:

inserting a guidewire into a blood vessel;

advancing a distal end of the guidewire within the blood vessel;

advancing at least part of an engagement catheter over the guidewire and into the blood vessel, wherein a distal end of the engagement catheter contacts the wall of the luminal organ;

providing suction through a lumen of the engagement catheter so that the distal end of the engagement catheter suctionally engages the wall of the luminal organ;

inserting at least part of a needle into the blood vessel of a patient, wherein the at least part of the needle is inserted into the at least part of the engagement catheter, which is then present within the blood vessel of the patient;

advancing a distal end of the needle within the blood vessel to a location adjacent to a wall of the luminal organ;

piercing the wall of the luminal organ using the needle so that a tip of the needle is present within the wall of the luminal organ;

injecting a substance through the needle and out of a distal portion of the needle while the suction is being provided through the lumen of the engagement catheter, so that at least some of the substance is present outside of the needle and inside of the wall of the luminal organ to reinforce the wall of the luminal organ; and withdrawing the distal portion of the needle from the wall of the luminal organ.

2. The method of claim 1, further comprising the step of:

removing any of the substance that may leak from the wall of the luminal organ after the distal portion of the needle is withdrawn from the wall of the luminal organ via suction through the lumen of the engagement catheter.

3. The method of claim 1, wherein the step of injecting is performed to inject a substance selected from the group consisting of stem cells, a polymer, an elastomer, a dug/medicament, cells other than stem cells, and a solution.

4. A method for reinforcing a wall of a luminal organ, comprising the steps of:

inserting a guidewire into a blood vessel;

advancing a distal end of the guidewire within the blood vessel;

advancing at least part of an engagement catheter over the guidewire and into the blood vessel while a sheath is at least partially present around the engagement catheter, and wherein the engagement catheter comprises a suction cup at a distal end and wherein movement of the sheath relative to the engagement catheter allows the suction cup to be exposed outside of the sheath so that the suction cup can expand;

inserting at least part of a needle into the blood vessel of a patient, wherein the at least part of the needle is inserted into the at least part of the engagement catheter, which is then present within the blood vessel of the patient;

advancing a distal end of the needle within the blood vessel to a location adjacent to a wall of the luminal organ;

piercing the wall of the luminal organ using the needle so that a tip of the needle is present within the wall of the luminal organ;

injecting a substance through the needle and out of a distal portion of the needle, so that at least some of the substance is present outside of the needle and inside of the wall of the luminal organ to reinforce the wall of the luminal organ; and withdrawing the distal portion of the needle from the wall of the luminal organ.

5. The method of claim 4, wherein the step of advancing the at least part of the engagement catheter over the guidewire and into the blood vessel is performed so that the suction cup of the engagement catheter contacts the wall of the luminal organ and further comprises the step of providing suction through a lumen of the engagement catheter so that the suction cup of the engagement catheter suctionally engages the wall of the luminal organ.

6. The method of claim 5, wherein when performing the step of injecting the substance through the needle and out of the distal portion of the needle, any substance that is injected out of the distal portion of the needle and not into the wall of the luminal organ would be removed from the patient via suction through the lumen of the engagement catheter.

7. The method of claim 5, further comprising the step of:
removing any of the substance that may leak from the wall of the luminal organ after the distal portion of the needle is withdrawn from the wall of the luminal organ via suction through the lumen of the engagement catheter.

8. The method of claim 4, wherein the step of injecting is performed to inject a substance selected from the group consisting of stem cells, a polymer, an elastomer, a dug/medicament, cells other than stem cells, and a solution.

9. A method for reinforcing a wall of a luminal organ, comprising the steps of:
inserting at least part of a needle into a blood vessel of a patient; wherein the needle has a first distal aperture defined within the needle at a distal tip of the needle along a relative sidewall of the needle, wherein the first distal aperture is relatively curved at a distal portion of the first distal aperture and tapers inward toward a distal portion of the first distal aperture;

advancing a distal end of the needle within the blood vessel to a location adjacent to a wall of the luminal organ;

piercing the wall of the luminal organ using the needle so that a tip of the needle is present within the wall of the luminal organ;

injecting a substance through the needle and out of the first distal aperture so that at least some of the substance is present outside of the needle and inside of the wall of the luminal organ to reinforce the wall of the luminal organ; and withdrawing the distal portion of the needle from the wall of the luminal organ.

10. The method of claim 9, further comprising the step of:
removing any of the substance that may leak from the wall of the luminal organ after the distal portion of the needle is withdrawn from the wall of the luminal organ via suction through the lumen of the engagement catheter.

11. The method of claim 9, wherein the step of injecting is performed to inject a substance selected from the group consisting of stem cells, a polymer, an elastomer, a dug/medicament, cells other than stem cells, and a solution.

12. A method for reinforcing a wall of a luminal organ, comprising the steps of:
inserting at least part of a needle into a blood vessel of a patient; wherein the needle has a curved distal portion and a first distal aperture defined within the needle along at least part of the curved distal portion;

advancing a distal end of the needle within the blood vessel to a location adjacent to a wall of the luminal organ;

piercing the wall of the luminal organ using the needle so that a tip of the needle is present within the wall of the luminal organ;

injecting a substance through the needle and out of the first distal aperture in a direction other than a direction defined by an axis of a portion of the needle proximal to the curved distal portion, so that at least some of the substance is present outside of the needle and inside of the wall of the luminal organ to reinforce the wall of the luminal organ; and withdrawing the distal portion of the needle from the wall of the luminal organ.

13. The method of claim 12, further comprising the step of:
removing any of the substance that may leak from the wall of the luminal organ after the distal portion of the needle is withdrawn from the wall of the luminal organ via suction through the lumen of the engagement catheter.

14. The method of claim 12, wherein the step of injecting is performed to inject a substance selected from the group consisting of stem cells, a polymer, an elastomer, a dug/medicament, cells other than stem cells, and a solution.

15. A method for reinforcing a wall of a luminal organ, comprising the steps of:
inserting at least part of a system into a blood vessel of a patient, the system comprising a needle positioned within a lumen of an engagement catheter having a suction cup at its distal end;

advancing the at least part of the engagement catheter within the blood vessel so that the suction cup of the engagement catheter contacts a wall of the luminal organ, while a sheath is at least partially present around the engagement catheter, and wherein movement of the sheath relative to the engagement catheter allows the suction cup to be exposed outside of the sheath so that the suction cup can expand;

providing suction through a lumen of the engagement catheter so that the suction cup of the engagement catheter suctionally engages the wall of the luminal organ;

piercing the wall of the luminal organ, while under suction through the lumen of the engagement catheter, using the needle so that a tip of the needle is present within the wall of the luminal organ;

injecting a substance through the needle and out of a distal portion of the needle so that at least some of the substance is present outside of the needle and inside of the wall of the luminal organ to reinforce the wall of the luminal organ.

16. The method of claim 15, wherein when performing the step of injecting the substance through the needle and out of the distal portion of the needle, any substance that is injected out of the distal portion of the needle and not into the wall of the luminal organ would be removed from the patient via suction through the lumen of the engagement catheter.

17. A method for reinforcing a wall of a luminal organ, comprising the steps of:

inserting at least part of a system into a blood vessel of a patient, the system comprising a needle positioned within a lumen of an engagement catheter having a suction cup at its distal end;

advancing the at least part of the engagement catheter within the blood vessel so that the suction cup of the engagement catheter contacts a wall of a myocardium;

providing suction through a lumen of the engagement catheter so that the suction cup of the engagement catheter suctionally engages the wall of the myocardium;

piercing the wall of the myocardium, while under suction through the lumen of the engagement catheter, using the needle so that a tip of the needle is present within the wall of the myocardium;

injecting a first substance through the needle and out of a distal portion of the needle so that at least some of the first substance is present outside of the needle and inside of the wall of the myocardium to reinforce the wall of the myocardium to treat the patient;

injecting a second substance through the needle and out of a distal portion of the needle so that at least some of the first substance is present outside of the needle and inside of the wall of the myocardium; and wherein the step of injecting is performed to inject the substance having a first ionic content, and wherein the step of injecting the second substance is performed in inject the second substance having a second ionic content differing from the first ionic content.

18. The method of claim 17, wherein the step of injecting is performed to inject a substance selected from the group consisting of stem cells, a polymer, an elastomer, a dug/medicament, cells other than stem cells, and a solution.

19. The method of claim 17, further comprising the step of:

removing any of the first substance that may leak from the wall of the myocardium after the distal portion of the needle is withdrawn from the wall of the wall of the myocardium via suction through the lumen of the engagement catheter.

20. The method of claim 17, further comprising the step of:

removing any of the second substance that may leak from the wall of the myocardium after the distal portion of the needle is withdrawn from the wall of the wall of the myocardium via suction through the lumen of the engagement catheter.

\* \* \* \* \*